US012760367B2

(12) United States Patent
Polymeropoulos et al.

(10) Patent No.: US 12,760,367 B2
(45) **Date of Patent: *Oct. 13, 2026**

(54) TREATMENT OF ATOPIC DERMATITIS WITH TRADIPITANT

(71) Applicant: VANDA PHARMACEUTICALS INC., Washington, DC (US)

(72) Inventors: Mihael H. Polymeropoulos, Potomac, MD (US); Changfu Xiao, Vienna, VA (US); Gunther Birznieks, Chevy Chase, MD (US); Andrew Heitman, Washington, DC (US); Sandra Smieszek, Cleveland, OH (US)

(73) Assignee: Vanda Pharmaceuticals Inc., Washington, DC (US)

( * ) Notice: Subject to any disclaimer, the term of this patent is extended or adjusted under 35 U.S.C. 154(b) by 881 days.

This patent is subject to a terminal disclaimer.

(21) Appl. No.: 17/981,739

(22) Filed: Nov. 7, 2022

(65) Prior Publication Data

US 2023/0073637 A1 Mar. 9, 2023

Related U.S. Application Data

(63) Continuation of application No. 16/644,567, filed as application No. PCT/US2018/048825 on Aug. 30, 2018, now Pat. No. 11,549,147.

(60) Provisional application No. 62/572,456, filed on Oct. 14, 2017, provisional application No. 62/558,303, filed on Sep. 13, 2017.

(51) Int. Cl.
*A61K 31/444* (2006.01)
*C12Q 1/6883* (2018.01)

(52) U.S. Cl.
CPC .......... *C12Q 1/6883* (2013.01); *A61K 31/444* (2013.01); *C12Q 2600/106* (2013.01); *C12Q 2600/156* (2013.01)

(58) Field of Classification Search
CPC ................ A61K 31/444; C12Q 1/6883; C12Q 2600/106; C12Q 2600/156
See application file for complete search history.

(56) References Cited

U.S. PATENT DOCUMENTS

| | | | |
|---|---|---|---|
| 5,585,385 | A | 12/1996 | Natsugari et al. |
| 6,329,394 | B1 | 12/2001 | Hagan et al. |
| 7,179,804 | B2 | 2/2007 | Amegadzie et al. |
| 7,320,994 | B2 | 1/2008 | Amegadzie et al. |
| 7,381,826 | B2 | 6/2008 | Borghese et al. |
| 7,799,782 | B2 | 9/2010 | Munson et al. |
| 8,772,496 | B2 | 7/2014 | Chen |
| 10,463,655 | B2 | 11/2019 | Polymeropoulos et al. |
| 10,772,880 | B2 | 9/2020 | Polymeropoulos et al. |
| 10,821,099 | B2 | 11/2020 | Polymeropoulos |
| 11,549,147 | B2 | 1/2023 | Polymeropoulos et al. |
| 2014/0378521 | A1 | 12/2014 | Zhang et al. |
| 2019/0216779 | A1 | 7/2019 | Basta et al. |

FOREIGN PATENT DOCUMENTS

| | | | |
|---|---|---|---|
| JP | 2006199614 | A | 8/2006 |
| JP | 2014193155 | A | 10/2014 |
| RU | 2724053 | C2 | 6/2019 |
| WO | 2007096782 | A2 | 8/2007 |
| WO | 2016195723 | A1 | 8/2016 |
| WO | 2016141341 | A1 | 9/2016 |
| WO | 2017060488 | A1 | 4/2017 |

OTHER PUBLICATIONS

Ardern-Jones., Exp. Dermatology, vol. 27, pp. 433-434, publ. Aug. 4, 2016 (Year: 2016).*

Mediaty, A et al. "Total and specific serum IgE decreases with age in patients with allergic rhinitis, asthma and insect allergy but not in patients with atopic dermatitis." Immunity & Ageing, 2005, 2 (1):9, doi:10.1186/1742-4933-2-9.

Masashi Amano, et al., Relationship between atopic dermatitis and serum TARC level, Tenri Medical Bulletin, vol. 13 (1): 39-47 (2010).

Miller, G. "Tackling Alcoholism With Drugs." Science, Apr. 11, 2008, vol. 320, No. 5873, pp. 168-170.

Sinha, R. et al. "Translational and reverse translational research on the role of stress in drugs craving and relapse." Psychopharmacology, Apr. 15, 2011, vol. 218, No. 1, pp. 69-82.

Notice of Reasons for Rejection for JP Application No. 2021-12356, Mailing No. 083985, mailed Sep. 17, 2024.

Yamamoto, Nobuharu et al., Effect of a novel NK1 receptor antagonist, fosaprepitant (Proemend®), used in patients with oral cancer treated with cisplatin, Oral Tumors 25(3): 109-114 (2013).

Folia Pharmacol. Jpn. (Nippon Yakurigaku Zasshi) 114, Suppl 1, 209P-214P (1999).

Director of New Drugs Division, Pharmaceutical Affairs Bureau, Ministry of Health and Welfare, General Guidelines for Clinical Evaluation of New Drugs, No. 43, addressed to the Chiefs of Health Administration Departments in each prefecture (Jun. 29, 1992).

Camilleri, M. et al., Gastroparesis, Nature Reviews: Disease Primers, Article Citation ID: (2018) 4:41; pp. 1-20 (Nov. 1, 2018).

Hagiwara, D., "Discovery of Low-Molecular Weight Antagonists of Substance P: Recent Developments and Prospects as a Therapeutic Agent," Journal of Synthetic Organic Chemistry (Japan), vol. 52, Issue 5, 1994, pp. 445-452.

Shinya Usui, Decision of Refusal, Japanese Patent Application No. 2021-012356 "Method of Treatment with Tradipitant", pp. 1-3 (Sep. 20, 2022).

Eichenfield et al., "Guidelines of care for the management of atopic dermatitis, Section 1. Diagnosis and assessment of atopic dermatitis," J. Am. Acad. Dermatol., 70:338-351, Feb. 2014, 14 pages.

Sidbury et al., "Guidelines of care for the management of atopic dermatitis, Section 3. Management and treatment with phototheraphy and systemic agents," J. Am. Acad. Dermatol., 71:327-349, Aug. 2014, 23 pages.

(Continued)

*Primary Examiner* — Sarah Pihonak
(74) *Attorney, Agent, or Firm* — Hoffman Warnick LLC

(57) ABSTRACT

The disclosure relates to improved methods of treatment of atopic dermatitis and symptoms thereof with tradipitant.

20 Claims, 10 Drawing Sheets

(56) References Cited

OTHER PUBLICATIONS

Mittermann et al., "IgE Sensitization Profiles Differ between Adult Patients with Severe and Moderate Atopic Dermatitis," Plos One, DOI: 10.1371/journal.pone.0156077, May 26, 2016, 15 pages.
Paternoster et al., "Multi-ancestry genome-wide association study of 21,000 cases and 95,000 controls identifies new risk loci for atopic dermatitis," Nature Genetics, vol. 47 (12), Dec. 2015, 10 pages.
Paternoster et al., Nature Genetics, publ. 2015, vol. 47(12), pp. 1449-1458 (Year: 2015).
Mittermann et al., PLos One., publ. 2016, vol. 11(5), pp. 1-15 (Year: 2016).
Masaki Futamura, MD, PhD, et al., "A systematic review of Investigator Global Assessment (IGA) in atopic dermatitis (AD) trials: Many options, no standards," Journal of the American Academy of Dermatology, vol. 74, No. 2, pp. 288-298 (Dec. 11, 2015).
Trower, "Neurokinin-1 receptor antagonist orvepitant is an effective inhibitor of itch-associated response in a Mongolian gerbil model of scratching behaviour," Experimental Dermatology; 2014; 23, pp. 853-864.
Santini, "Aprepitant for management of severe pruritus related to biological cancer treatments: a pilot study," The Lancet; vol. 13; Oct. 2012; Published online Sep. 18, 2012; pp. 1020-1024.
FDA; "Guidance for Industry Exposure-Response Relationships—Study Design, Data Analysis, and Regulatory Applications;" Published Apr. 2003; pp. 1-28.
Sun et al., "Particle Size Specifications for Solid Oral Dosage Forms: A Regulatory Perspective;" American Pharmaceutical Review, Published May 1, 2010; pp. 1-9.
Sadick Research Group; "Tradipitant in Treatment-Resistant Pruritus Associated With Atopic Dermatitis;" ClinicalTrials.gov Identifier NCT02672410; First Received Feb. 1, 2016; last Updated Feb. 2, 2016; accessed on Feb. 11, 2016; pp. 3; <https://clinicaltrials.gov/ct2/show/study/NCT02672410?TERM=TRADIPITANT&RANK=3>.
George et al., "Supporting Online Material for Neurokinin 1 Receptor Antagonism as a Possible Therapy for Alcoholism," Science, vol. 319, No. 2869, dated Mar. 14, 2008, 14 pages.
George et al., "Neurokinin 1 Receptor Antagonism as a Possible Therapy for Alcholism;" Science, vol. 319, No. 2869, dated Mar. 14, 2008, 6 pages.
Stander et al., "Targeting the Neurokinin Receptor 1 with Aprepitant: A Novel Antipruritic Strategy," Plos One, vol. 6., No. 6, Jan. 1, 2010, 6 pages.
Tauscher et al., "Development of the 2nd generation neurokinin-1 receptor antagonist LY686017 for social anxiety disorder," European Neuropsychopharmacology; 2010; Elsevier Science Publishers BV, Amsterdam, NL, vol. 20, No. 2, Feb. 1, 2010, 8 pages.
Anonymous, "History of Changes for Study: NCT02004041: Proof of Concept of VLY-686 in Subjects With Treatment—Resistant Pruritus Associated with Atopic Dermatitis," U.S. National Library of Medicine, ClinicalTrials.gov archive, retrieved from: https://clinicaltrials.gov/ct2/history/NCT02004041?A=4&B=4&C=merged on Dec. 16, 2019, 9 pages.
Anonymous, "History of Changes for Study: NCT01919944: Study of Itch Control by VLY-686 in Healthy Volunteers After Intradermal Injections of Substance P," U.S. National Library of Medicine, ClinicalTrials.gov archive, retrieved from: https://clinicaltrials.gov/ct2/history/NCT01919944?A=5&B=5&C=merged on Dec. 16, 2019, 9 pages.
Sonja Stander et al., "An Investigational Study of Tradipitant For the Treatment of Chronic Pruritus in Patients With Atopic Dermatitis," Acta Dermato-Venereologica 2015 Medical Journals/Acta D-V NLD; vol. 95; No. 7; 2015; XP002786610; ISSN: 1651-2057; Abstract.
International Search Report and Written Opinion for corresponding PCT Application No. PCT/US2018/048825 dated Mar. 12, 2018, 13 pages.

* cited by examiner

TREATMENT OF ATOPIC DERMATITIS WITH TRADIPITANT

CROSS REFERENCE TO RELATED APPLICATIONS

This patent application is a continuation of U.S. application Ser. No. 16/644,567, filed Mar. 5, 2020, which is a US national phase under 35 USC 371 of international patent application no. PCT/US2018/048825, filed Aug. 30, 2018, which claims the benefit of U.S. provisional patent application No. 62/558,303, filed on Sep. 13, 2017, and U.S. provisional patent application No. 62/572,456, filed on Oct. 14, 2017.

BACKGROUND

Atopic dermatitis (AD) is a common, chronic, and relapsing inflammatory skin disorder caused by a hypersensitivity reaction in the skin, and characterized by the symptom of intense and persistent pruritus or itch, which may be localized or even generalized, and may not be relieved by scratching. Other clinical features include erythema, excoriation, edema, lichenification, oozing, and xerosis. Scratching due to the itching may contribute to raw, sensitive, swollen skin, and render skin susceptible to infection. AD is also known as atopic eczema or eczema, and frequently presents during childhood.

Immunoglobulin E (IgE)-mediated allergy plays a central role in the pathophysiology of atopic dermatitis and other clinical phenotypes such as asthma and food allergy. Atopy and plasma IgE concentration are genetically complex traits, and the specific genetic risk factors that lead to IgE dysregulation and clinical atopy are an area of active investigation.

Other genes are also involved in the atopic dermatitis phenotype. CTNNA3 encodes a structural cadherin that is important for cell-cell adhesion. CTNNA3 is also important in allergy and asthma. Reduced CTNNA3 levels are found in the bronchial biopsies of asthmatics, and are correlated inversely with eosinophil numbers. Variants in CTNNA3 have been associated with response to glucocorticoid therapy in childhood asthma in a genome-wide association study (GWAS).

INADL is a gene that encodes a protein with multiple PDZ domains that localize to tight junctions and to the apical membrane of epithelial cells. Tight junction defects have been shown in patients with atopic dermatitis; specifically, tight junctions reside immediately below the stratum corneum and regulate the selective permeability of the paracellular pathway.

Chronic pruritus, including that caused by AD, represents a serious and unmet medical need. The itch sensation is believed to be induced at least in part through the action of the endogenous neuropeptide substance P (SP), through the binding at NK-1Rs expressed on multiple skin cells.

The NK-1R is expressed throughout different tissues of the body, with major activity found in neuronal tissue. SP and NK-1R interactions in neuronal tissue regulate neurogenic inflammation locally and the pain perception pathway through the central nervous system. Other tissues, including endothelial cells and immune cells, have also exhibited SP and NK-1R activity. The activation of NK-1R by the natural ligand SP is involved in numerous physiological processes, including the perception of pain, behavioral stressors, cravings, and the processes of nausea and vomiting. An inappropriate over-expression of SP either in nervous tissue or peripherally could result in pathological conditions such as substance dependence, anxiety, nausea/vomiting, and pruritus. An NK-1R antagonist may possess the ability to reduce this over-stimulation of the NK-1R, and as a result address the underlying pathophysiology of the symptoms in these conditions.

Tradipitant is a potent and selective neurokinin-1 receptor antagonist formerly known as VLY-686, having the chemical names 2-[1-[[3,5-bis(trifluoromethyl)phenyl]methyl]-5-(4-pyridinyl)-1H-1,2,3-triazol-4-yl]-3-pyridinyl](2-chlorophenyl)-methanone and {2-[1-(3,5-Bistrifluoromethylbenzyl)-5-pyridin-4-yl-1H-[1,2,3]triazol-4-yl]-pyridin-3-yl}-(2-chlorophenyl)-methanone, and the following chemical structure:

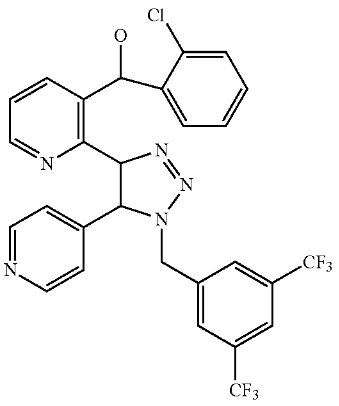 [SMILES: OC(c1ccccc1Cl)c1cccnc1C1N=NN(Cc2cc(C(F)(F)F)cc(C(F)(F)F)c2)C1c1ccncc1]

Tradipitant is disclosed in U.S. Pat. No. 7,320,994, and contains six main structural components: the 3,5-bis-trifluoromethylphenyl moiety, two pyridine rings, the triazol ring, the chlorophenyl ring and the methanone. Crystalline Forms IV and V of tradipitant are disclosed in U.S. Pat. No. 7,381,826. A process for synthesizing tradipitant is disclosed in U.S. Pat. Nos. 8,772,496; 9,708,291; and 10,035,787.

BRIEF DESCRIPTION OF THE INVENTION

Various aspects of the invention disclosed herein related to improved methods for treating pruritus or atopic dermatitis in an individual in need thereof by administering tradipitant in amounts effective for such treatment. One such improvement provides that the patient may be selected for treatment based upon a determination that the patient's genotype includes a genotype that is associated with a high IgE level or a positive tradipitant treatment response otherwise. Specifically, in a method consisting of administering an amount of tradipitant effective to treat a patient with pruritus or atopic dermatitis, one aspect of the invention is the improvement comprising selecting the patient for treatment based upon a determination that the patient's genotype includes a genotype associated with a high IgE level or a positive tradipitant treatment response.

In this regard, the genotype associated with a high IgE level may be selected from the group consisting of: rs4575660 TT, rs276555 CC, rs74416548 ATAT, rs276556 GG, rs276560 CC, rs276561 TT, rs276562 GG, rs276563 CC, rs276564 GG, rs276571 GG, rs140796 TATTGTATTG, rs276573 TT, rs276574 GG, rs4895474 TT, rs4895475 GG, rs9483989 TT, rs9373178 CC, rs4896234 CC, rs2327798 GG, rs62420823 GG, rs17252967 CC, rs9494657 AA, rs9402871 GG, rs9402872 CC, rs9399201 GG, rs4896235

AA, rs719640 AA, rs9373179 AA, rs9385784 TT, rs2146275 AA, rs6941440 TT, rs4896237 TT, rs6929580 GG, rs4896239 TT, rs4895479 CC, rs4895480 TT, rs4280975 GG, rs6911523 AA, rs6912319 GG, rs2280090 non-GG, and rs57930837 non-AA.

In addition, the genotype associated with a positive tradipitant treatment response may be selected from the group consisting of: rs16847120 GG, rs249122 AA, rs6862796 CC, rs249137 TT, rs249138 TT, rs144713688 GAGAA, rs73258486 GG/GA, rs6480251 CC/CT, rs6480252 TT/TC, rs10822978 TT/TA, rs10997525 GG/GA, rs10997527 CC/CA, rs7074325 CC/CT, rs57930837 CC/CA, rs11453660 CACA/CAC, rs2199792 AA/AG, rs4963245 non-CC, rs12990449 non-TT, rs727162 non-CC, rs58161637 non-GG, rs62622847 non-CC, rs3213755 non-AA, rs41521946 non-TT, rs28362678 non-AA, rs35624343 non-AA, rs28362677 non-TT, rs11207832 non-CC, rs1954436 non-CC, rs11207834 non-CC, rs370530530 non-CTCT, rs11207838 non-TT, rs150980554 non-AA, rs7551886 non-CC, rs6664979 non-CC, rs12043665 non-AA, rs12030784 non-TT, rs79037385 non-GG, rs74568317 non-CC, rs3790575 non-CC, and rs77939406 non-GG.

Another aspect of the present invention, in a method consisting of administering an amount of tradipitant effective to treat a patient with pruritus or atopic dermatitis, includes the improvement comprising selecting the patient for such treatment based upon a determination that the patient has a level of IgE of greater than or equal to 50 kU/L. Alternatively, this improvement is carried out wherein the patient has a level of IgE of greater than or equal to: 75 kU/L, 100 kU/L, 150 kU/L, 200 kU/L, or 300 kU/L. In any event, such improved methods above may be practiced by internally administering tradipitant to such a patient at a dose of 100-400 mg/day or 100-300 mg/day or 100-200 mg/day. Specifically, the daily dose may comprise internally administering tradipitant to the patient at a dose of 85 mg bid.

The present invention further provides an improved method for treating a patient suffering from pruritus or atopic dermatitis with tradipitant comprising, first, selecting a dosage effective for treating the patient based upon identifying the patient's genotype at one or more SNP that is associated with IgE level or with tradipitant treatment effect, and then:

- if the patient has a genotype associated with a high IgE level or with a positive response to treatment with tradipitant, then internally administering tradipitant to the patient at a dosage effective to treat pruritus or atopic dermatitis in the patient that would have been selected absent the identification of the patient's genotype, and
- if the patient has a genotype that is not associated with a high IgE level or a positive response to treatment with tradipitant, then internally administering tradipitant to the patient at a dosage that is higher than the dosage that would otherwise have been selected for the patient absent the identification of the patient's genotype.

The foregoing method may be practiced by identifying the patient's genotype at a SNP that is associated with a high IgE level, and the SNP is selected from the group consisting of: rs4575660, rs276555, rs74416548, rs276556, rs276560, rs276561, rs276562, rs276563, rs276563, rs276564, rs276564, rs276571, rs140796, rs276573, rs276574, rs4895474, rs4895475, rs9483989, rs9373178, rs4896234, rs2327798, rs62420823, rs17252967, rs9494657, rs9402871, rs9402872, rs9399201, rs4896235, rs719640, rs9373179, rs9385784, rs2146275, rs6941440, rs4896237, rs6929580, rs4896239, rs4895479, rs4895480, rs4280975, rs6911523, rs6912319, rs2280090, and rs57930837.

For example, this method may be practiced wherein the genotype associated with a high IgE level is selected from the group consisting of: rs4575660 TT, rs276555 CC, rs74416548 ATAT, rs276556 GG, rs276560 CC, rs276561 TT, rs276562 GG, rs276563 CC, rs276564 GG, rs276571 GG, rs140796 TATTGTATTG, rs276573 TT, rs276574 GG, rs4895474 TT, rs4895475 GG, rs9483989 TT, rs9373178 CC, rs4896234 CC, rs2327798 GG, rs62420823 GG, rs17252967 CC, rs9494657 AA, rs9402871 GG, rs9402872 CC, rs9399201 GG, rs4896235 AA, rs719640 AA, rs9373179 AA, rs9385784 TT, rs2146275 AA, rs6941440 TT, rs4896237 TT, rs6929580 GG, rs4896239 TT, rs4895479 CC, rs4895480 TT, rs4280975 GG, rs6911523 AA, rs6912319 GG, rs2280090 non-GG, and rs57930837 non-AA.

Alternatively, this method may be practiced by identifying the patient's genotype at a SNP that is associated with a positive response to treatment with tradipitant, and the SNP is selected from the group consisting of: rs16847120, rs249122, rs6862796, rs249137, rs249138, rs144713688, rs73258486, rs6480251, rs6480252, rs10822978, rs10997525, rs10997527, rs7074325, rs57930837, rs11453660, rs2199792, rs4963245, rs12990449, rs727162, rs58161637, rs62622847, rs3213755, rs41521946, rs28362678, rs35624343, rs28362677, rs11207832, rs1954436, rs11207834, rs370530530, rs11207838, rs150980554, rs7551886, rs6664979, rs12043665, rs12030784, rs79037385, rs74568317, rs3790575, and rs77939406.

Alternatively, the foregoing method may be practiced wherein the genotype associated with a positive response to treatment with tradipitant is selected from the group consisting of: rs16847120 GG, rs249122 AA, rs6862796 CC, rs249137 TT, rs249138 TT, rs144713688 GAGAA, rs73258486 GG/GA, rs6480251 CC/CT, rs6480252 TT/TC, rs10822978 TT/TA, rs10997525 GG/GA, rs10997527 CC/CA, rs7074325 CC/CT, rs57930837 CC/CA, rs11453660 CACA/CAC, rs2199792 AA/AG, rs4963245 non-CC, rs12990449 non-TT, rs727162 non-CC, rs58161637 non-GG, rs62622847 non-CC, rs3213755 non-AA, rs41521946 non-TT, rs28362678 non-AA, rs35624343 non-AA, rs28362677 non-TT, rs11207832 non-CC, rs1954436 non-CC, rs11207834 non-CC, rs370530530 non-CTCT, rs11207838 non-TT, rs150980554 non-AA, rs7551886 non-CC, rs6664979 non-CC, rs12043665 non-AA, rs12030784 non-TT, rs79037385 non-GG, rs74568317 non-CC, rs3790575 non-CC, and rs77939406 non-GG.

Another aspect of the invention relates to a method for treating a patient with pruritus or atopic dermatitis by administering an amount of tradipitant effective for such treatment, comprising selecting a dosage effective for treating the patient based upon identifying the patient's baseline IgE level; and

- if the patient has a baseline IgE level greater than about 100 kU/L, then internally administering tradipitant to the patient at a dosage effective to treat pruritus or atopic dermatitis in the patient that would have been selected absent the identification of the patient's baseline IgE, and
- if the patient does not have a baseline IgE level greater than about 100 kU/L, then internally administering tradipitant to the patient at a dosage that is higher than the dosage that would otherwise have been selected for the patient absent the identification of the patient's baseline IgE.

The foregoing method may further involve identifying the patient's baseline IgE level by testing a biological sample from the patient to determine an amount of IgE in the biological sample. In addition, the methods above result in differential dosages based upon genotype, including dosing a patient receiving a higher dosage of tradipitant with an amount that is from greater than 170 mg/day to 340 mg/day internally administered, more specifically from greater than 170 mg/day to 255 mg/day. More particularly, the amount that is greater than 170 mg/day may be, e.g., about 25% greater than 170 mg/day. As one example of dosage selection, a patient identified with a baseline IgE level greater than about 100 kU/L has a dosage selected of 170 mg/day, e.g., 85 mg bid.

In yet another aspect of the present invention, a method is provided for selecting a dosage of tradipitant effective for treatment of a patient suffering from atopic dermatitis, comprising:

(1) identifying a genotype of the patient at one or more SNPs selected from the group consisting of: rs4575660, rs276555, rs74416548, rs276556, rs276560, rs276561, rs276562, rs276563, rs276563, rs276564, rs276564, rs276571, rs140796, rs276573, rs276574, rs4895474, rs4895475, rs9483989, rs9373178, rs4896234, rs2327798, rs62420823, rs17252967, rs9494657, rs9402871, rs9402872, rs9399201, rs4896235, rs719640, rs9373179, rs9385784, rs2146275, rs6941440, rs4896237, rs6929580, rs4896239, rs4895479, rs4895480, rs4280975, rs6911523, rs6912319, rs2280090, rs57930837, rs4963245, rs12990449, rs727162, rs58161637, rs62622847, rs3213755, rs41521946, rs28362678, rs35624343, rs28362677, and rs11207834; and (2) selecting a dosage of about 170 mg/day if:

(A) the patient's genotype includes one or more variants associated with a high IgE, selected from the group consisting of: rs4575660 TT, rs276555 CC, rs74416548 ATAT, rs276556 GG, rs276560 CC, rs276561 TT, rs276562 GG, rs276563 CC, rs276564 GG, rs276571 GG, rs140796 TATTGTATTG, rs276573 TT, rs276574 GG, rs4895474 TT, rs4895475 GG, rs9483989 TT, rs9373178 CC, rs4896234 CC, rs2327798 GG, rs62420823 GG, rs17252967 CC, rs9494657 AA, rs9402871 GG, rs9402872 CC, rs9399201 GG, rs4896235 AA, rs719640 AA, rs9373179 AA, rs9385784 TT, rs2146275 AA, rs6941440 TT, rs4896237 TT, rs6929580 GG, rs4896239 TT, rs4895479 CC, rs4895480 TT, rs4280975 GG, rs6911523 AA, rs6912319 GG, rs2280090 non-GG, and rs57930837 non-AA; or (B) one or more variants associated with positive tradipitant treatment response, selected from the group consisting of: rs16847120 GG, rs249122 AA, rs6862796 CC, rs249137 TT, rs249138 TT, rs144713688 GAGAA, rs73258486 GG/GA, rs6480251 CC/CT, rs6480252 TT/TC, rs10822978 TT/TA, rs10997525 GG/GA, rs10997527 CC/CA, rs7074325 CC/CT, rs57930837 CC/CA, rs11453660 CACA/CAC, rs2199792 AA/AG, rs4963245 non-CC, rs12990449 non-TT, rs727162 non-CC, rs58161637 non-GG, rs62622847 non-CC, rs3213755 non-AA, rs41521946 non-TT, rs28362678 non-AA, rs35624343 non-AA, rs28362677 non-TT, rs11207832 non-CC, rs1954436 non-CC, rs11207834 non-CC, rs370530530 non-CTCT, rs11207838 non-TT, rs150980554 non-AA, rs7551886 non-CC, rs6664979 non-CC, rs12043665 non-AA, rs12030784 non-TT, rs79037385 non-GG, rs74568317 non-CC, rs3790575 non-CC, and rs77939406 non-GG; or (3) selecting a dosage of greater than about 170 mg/day if the patient's genotype does not include a variant associated with a high IgE or with a positive tradipitant treatment response.

The present invention also includes a method for determining a dosage of tradipitant effective to treat a patient suffering from atopic dermatitis, whose baseline IgE level has been identified, comprising selecting a dosage of about 170 mg/day if the patient has a baseline IgE level greater than about 100 kU/L, or a dosage of greater than 170 mg/day if the patient does not have a baseline IgE level greater than about 100 kU/L. Similarly the present invention includes a method of determining that a patient is likely to respond to treatment of atopic dermatitis with tradipitant, comprising:

(1) identifying a genotype of the patient at one or more SNPs selected from the group consisting of: rs4575660, rs276555, rs74416548, rs276556, rs276560, rs276561, rs276562, rs276563, rs276563, rs276564, rs276564, rs276571, rs140796, rs276573, rs276574, rs4895474, rs4895475, rs9483989, rs9373178, rs4896234, rs2327798, rs62420823, rs17252967, rs9494657, rs9402871, rs9402872, rs9399201, rs4896235, rs719640, rs9373179, rs9385784, rs2146275, rs6941440, rs4896237, rs6929580, rs4896239, rs4895479, rs4895480, rs4280975, rs6911523, rs6912319, rs2280090, rs57930837, rs4963245, rs12990449, rs727162, rs58161637, rs62622847, rs3213755, rs41521946, rs28362678, rs35624343, rs28362677, and rs11207834; and (2) determining the patient is likely to respond to said treatment if the patient's genotype includes one or more variants selected from: rs4575660 TT, rs276555 CC, rs74416548 ATAT, rs276556 GG, rs276560 CC, rs276561 TT, rs276562 GG, rs276563 CC, rs276564 GG, rs276571 GG, rs140796 TATTGTATTG, rs276573 TT, rs276574 GG, rs4895474 TT, rs4895475 GG, rs9483989 TT, rs9373178 CC, rs4896234 CC, rs2327798 GG, rs62420823 GG, rs17252967 CC, rs9494657 AA, rs9402871 GG, rs9402872 CC, rs9399201 GG, rs4896235 AA, rs719640 AA, rs9373179 AA, rs9385784 TT, rs2146275 AA, rs6941440 TT, rs4896237 TT, rs6929580 GG, rs4896239 TT, rs4895479 CC, rs4895480 TT, rs4280975 GG, rs6911523 AA, rs6912319 GG, rs2280090 non-GG, and rs57930837 non-AA; or one or more variants associated with positive tradipitant treatment response selected from the group consisting of:

rs16847120 GG, rs249122 AA, rs6862796 CC, rs249137 TT, rs249138 TT, rs144713688 GAGAA, rs73258486 GG/GA, rs6480251 CC/CT, rs6480252 TT/TC, rs10822978 TT/TA, rs10997525 GG/GA, rs10997527 CC/CA, rs7074325 CC/CT, rs57930837 CC/CA, rs11453660 CACA/CAC, rs2199792 AA/AG, rs4963245 non-CC, rs12990449 non-TT, rs727162 non-CC, rs58161637 non-GG, rs62622847 non-CC, rs3213755 non-AA, rs41521946 non-TT, rs28362678 non-AA, rs35624343 non-AA, rs28362677 non-TT, rs11207832 non-CC, rs1954436 non-CC, rs11207834 non-CC, rs370530530 non-CTCT, rs11207838 non-TT, rs150980554 non-AA, rs7551886 non-CC, rs6664979 non-CC, rs12043665 non-AA, rs12030784 non-TT, rs79037385 non-GG, rs74568317 non-CC, rs3790575 non-CC, and rs77939406 non-GG.

Similarly, the present invention includes a method for identifying a patient whose IgE level has been identified as likely to respond to treatment of atopic dermatitis with tradipitant, comprising determining the patient is likely to respond to tradipitant treatment if the patient's baseline IgE level is greater than about 100 kU/L.

Based on the foregoing, the present invention has numerous aspects that can be described as follows:

In a first aspect of the invention, an improved method is provided for treating pruritus or atopic dermatitis in an individual in need thereof being internally administering tradipitant.

In a second aspect of the invention, a method is provided that comprises treating pruritus and/or atopic dermatitis in an individual in need thereof by internally administering tradipitant to the individual. In the method, the patient may be selected for treatment based upon a determination that the patient has a level of IgE that is greater than or equal to a threshold that may be, e.g., 50 kU/L, 75 kU/L, 100 kU/L, 150 kU/L, 200 kU/L, or 300 kU/L.

In either the first or the second aspect, the dose of tradipitant may be, e.g., 100-400 mg/day, 100-300 mg/day, 100-200 mg/day, or about 170 mg/day, which may be administered as 85 mg bid.

In a third aspect of the invention, a method is provided for treating a patient with tradipitant, wherein the patient is suffering from pruritus and/or atopic dermatitis. The method comprises the steps of: identifying the patient's genotype at one or more SNP that is associated with IgE level or with tradipitant treatment effect; and if the patient has a genotype associated with a high IgE level or with a positive response to treatment with tradipitant, then internally administering tradipitant to the patient at a first dosage; and if the patient has a genotype that is not associated with a high IgE level or with a positive response to treatment with tradipitant, then internally administering tradipitant to the patient at a second dosage that is greater than the first dosage, or internally administering an active pharmaceutical ingredient other than tradipitant.

In a fourth aspect of the invention, a method is provided for treating a patient with tradipitant, wherein the patient is suffering from pruritus and/or atopic dermatitis. The method comprises the steps of: identifying the patient's baseline IgE level; and if the patient has a baseline level of IgE that is greater than or equal to a threshold that may be, e.g., 50 kU/L, 75 kU/L, 100 kU/L, 150 kU/L, 200 kU/L, or 300 kU/L, then internally administering tradipitant to the patient at a first dosage, and if the patient does not have a baseline IgE level greater than the threshold, then internally administering tradipitant to the patient at a second dosage that is greater than the first dosage, or internally administering an active pharmaceutical ingredient other than tradipitant. In various embodiments, the first dosage may be about 170 mg/day, which may be administered as 85 mg bid, and the second dosage may be, e.g., about >170-340 mg/day, or about >170-255 mg/day.

In a fifth aspect of the invention, a method is provided for selecting a dosage of tradipitant for treatment of a patient suffering from atopic dermatitis, comprising: identifying a genotype of the patient at one or more SNPs associated with a high IgE level or with a positive tradipitant treatment response, wherein the dosage is about 170 mg/day if the patient's genotype includes one or more variants associated with a high IgE level; and the dosage is greater than about 170 mg/day if the patient's genotype does not include a variant associated with a high IgE or with a positive tradipitant treatment response.

In a sixth aspect of the invention, a method is provided for selecting a dosage of tradipitant for treatment of a patient suffering from atopic dermatitis, comprising: identifying a baseline IgE level for the patient, wherein the dosage is about 170 mg/day if the patient's baseline IgE is equal to or greater than a threshold level such as, e.g., 50 kU/L, 75 kU/L, 100 kU/L, 150 kU/L, 200 kU/L, or 300 kU/L; and the dosage is greater than about 170 mg/day if the patient's baseline IgE is lower than the threshold level.

In a seventh aspect of the invention, a method is provided for predicting whether a patient is likely to respond to treatment of atopic dermatitis and/or pruritus with tradipitant, comprising: identifying a genotype of the patient at one or more SNPs associated with a high IgE or with a positive tradipitant treatment response, wherein the patient is likely to respond to said tradipitant treatment if the patient's genotype includes one or more variants associated with a high IgE; and the patient is unlikely to respond to said treatment if the patient's genotype does not include a variant associated with a high IgE or with a positive tradipitant treatment response.

In an eighth aspect of the invention, a method is provided for predicting whether a patient is likely to respond to treatment of atopic dermatitis and/or pruritus with tradipitant, comprising: identifying a baseline IgE level for the patient, wherein the patient is likely to respond to said tradipitant treatment if the patient's baseline IgE is equal to or greater than a threshold level such as, e.g., 50 kU/L, 75 kU/L, 100 kU/L, 150 kU/L, 200 kU/L, or 300 kU/L; and the patient is unlikely to respond to said treatment if the patient's baseline IgE is lower than the threshold level.

DETAILED DESCRIPTION OF THE DISCLOSURE

Figure 1:
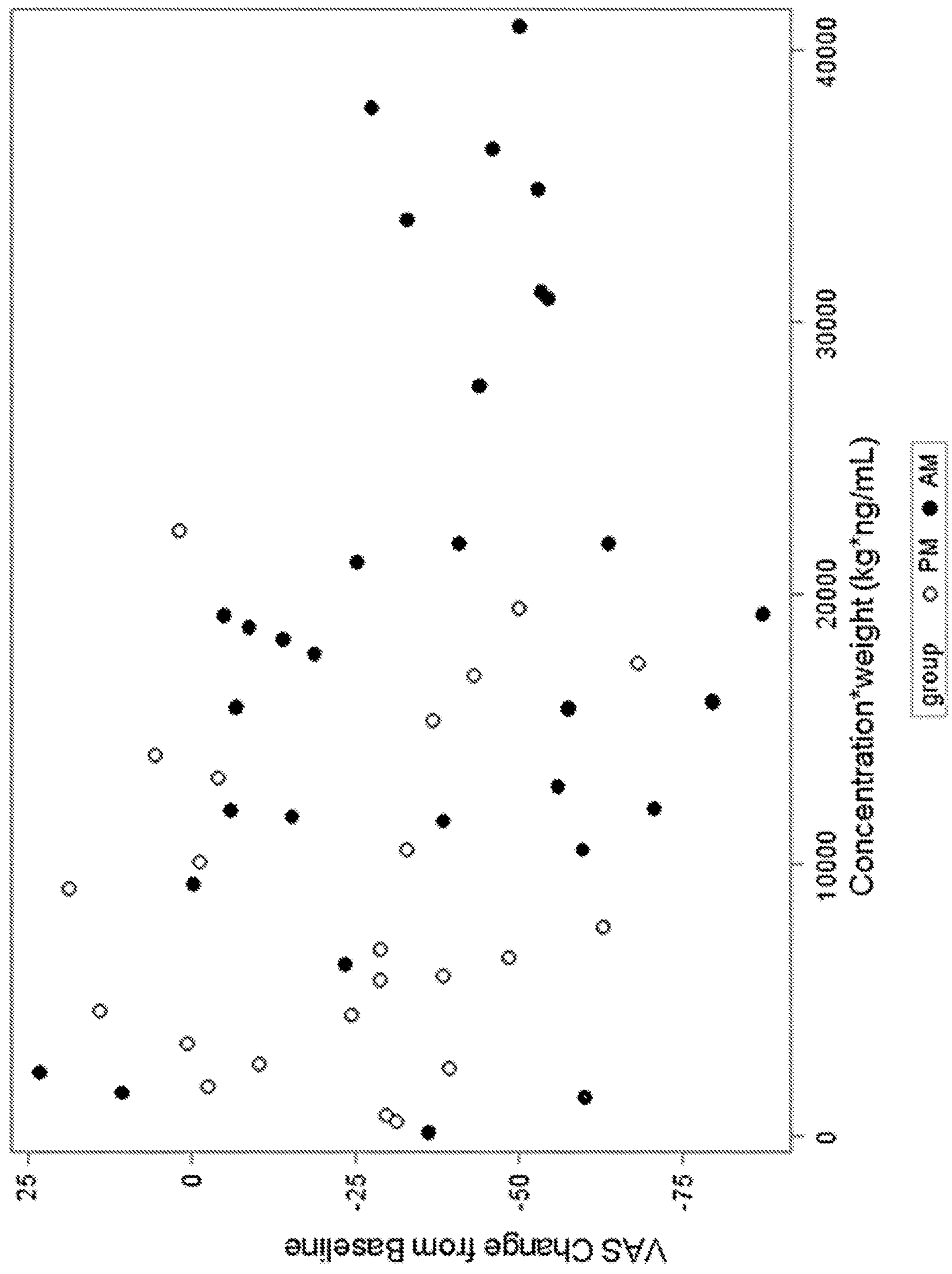
FIG. 1 provides a scatter plot of VAS change vs. concentration-weight of tradipitant (Spearman correlation P-value=0.0204), as described in Example 1.

In various embodiments of the invention, the improved methods described herein include methods for treating pruritus and/or atopic dermatitis using tradipitant, methods for selecting a dosage of tradipitant for use in the treatment of a patient suffering from atopic dermatitis and/or pruritus, and methods of determining that a patient is likely to respond to tradipitant treatment for atopic dermatitis and/or pruritus.

A method of using tradipitant to treat atopic dermatitis and/or pruritus in a patient may include first identifying the patient's genotype at one or more SNPs that are associated with one or both of IgE level or tradipitant treatment effect. As illustrated in the Examples below, baseline Immunoglobulin E (IgE) level is associated with tradipitant treatment effect. For this reason, genetic modifiers of IgE may also be considered markers for tradipitant treatment effect. Additionally, a number of genetic markers are identified herein which are directly associated with tradipitant treatment effect independently of IgE level. Examples of such SNPs are presented herein, for example in tables 8, 10, 11, and 12.

The identifying step may include a number of different methods of identification. In one aspect, identifying a genotype may include performing a genotyping assay on a biological sample collected from the patient to be treated. The biological sample may include, e.g., blood, serum, saliva, urine, et al. as is known in the art. In another aspect, identifying a genotype may include reviewing a patient's medical history, result report, or other document containing the result of a previously-performed assay or genetic test. In still further aspects, the identifying may include causing or requesting an assay to be performed by another individual, or causing or requesting the review of the patient's medical history, result report, or other document containing the result of a previously-performed assay or genetic test.

In the event that the patient's genotype at one of the indicated SNPs is associated with one or both of high Immunoglobulin E (IgE) level or with significant tradipitant treatment effect, the method further includes internally administering tradipitant to the patient at a first dosage. The first dosage may be, e.g., 100 to 400 mg/day, 100 to 300 mg/day, 100 to 200 mg/day, or about 85-170 mg/day, which may be administered as, e.g., 50 to 200 mg bid, 50 to 150 mg bid, 50 to 100 mg bid, or about 85 mg bid.

In the event that the patient's genotype is not associated with either of a high IgE level or significant tradipitant treatment effect at any of the indicated SNPs, the method includes alternative treatment. Such alternative treatment may include, for example, internal administration of tradipitant at a second dosage that is greater than the first dosage. For example, the second dosage may be 150%, 200%, 250%, or 300% of the first dosage, or may be from greater than 170 mg/day to 255 mg/day, or greater than 170 mg/day to 340 mg/day. Greater than 170 mg/day may mean, e.g., 25% greater. Such increased dosages may be accompanied by increased patient monitoring. In other embodiments, the alternative treatment may include internally administering an active pharmaceutical ingredient other than tradipitant.

Another method of using tradipitant to treat atopic dermatitis and/or pruritus in a patient may include first identifying the patient's baseline IgE level. The patient's IgE level may be identified, for example, by obtaining a biological sample from the patient and quantifying an amount of IgE present in the biological sample. The biological sample may be, e.g., a blood sample, serum sample, or similar as may be known in the art.

In both itch and disease severity, a consistently stronger treatment effect is observed among patients having a high IgE level compared to a low IgE level, regardless of the specific cutoff used to delineate high vs. low IgE levels. For example, this association is observed regardless of whether the high IgE group is defined by being greater than a threshold that is, e.g., 75 kU/L, 100 kU/L, 150 kU/L, 200 kU/L, or 300 kU/L, and whether the low IgE group is defined by being less than a threshold that is, e.g., 75 kU/L, 100 kU/L, 150 kU/L, 200 kU/L, or 300 kU/L. Any of these definitions of high or low IgE level may be used to practice the present invention.

If the patient is determined to have a high IgE level, for example an IgE level greater than or equal to a threshold that is 50 kU/L, 75 kU/L, 100 kU/L, 150 kU/L, 200 kU/L, or 300 kU/L, the patient can be expected to demonstrate a significant tradipitant treatment effect. Such patient may be internally administered tradipitant at a first dosage. However, if the patient has a baseline IgE level that is below the selected threshold, e.g., less than 50 kU/L, less than 75 kU/L, less than 100 kU/L, less than 150 kU/L, less than 200 kU/L, or less than 300 kU/L, then the patient may be internally administered tradipitant at a second dosage that is greater than the first dosage, or may be internally administered an active pharmaceutical ingredient other than tradipitant. The first dosage and second dosage may be substantially as previously described.

Methods of selecting a dosage of tradipitant for treatment of a patient suffering from atopic dermatitis and/or pruritus are also disclosed herein. Such a method may include identifying a genotype of the patient at one or more SNPs described herein as being associated with one or both of IgE level or tradipitant treatment effect, or alternatively, identifying the patient's IgE level. The methods of identifying said genotype or IgE level may include those methods previously discussed. Based on the identification or determination of the individual's genotype or IgE level, a dosage may be selected for the particular patient. For example, if the patient's genotype includes one or more variants associated with a high IgE or with a positive tradipitant treatment response, or if the patient's IgE level is identified as being greater than a threshold value, for example, 50 kU/L, 75 kU/L, 100 kU/L, 150 kU/L, 200 kU/L, or 300 kU/L, then a dosage of about 170 mg/day may be selected for the patient. Such dosage may more particularly be, for example, 85 mg bid. If the patient's IgE level is identified as being below a threshold value, for example, below 50 kU/L, 75 kU/L, 100 kU/L, 150 kU/L, 200 kU/L, or 300 kU/L, then a dosage of greater than about 170 mg/day may be selected for the patient. Such dosage may be, for example, 150%, 200%, 250%, or 300% of the first dosage of about 170 mg/day. Thus, the dosage may be, for example, from greater than about 170 mg/day to 255 mg/day, or from greater than about 170 mg/day to 340 mg/day.

Methods of predicting whether a patient is likely to respond to treatment of atopic dermatitis with tradipitant are further disclosed herein. Such methods may include identifying a genotype of the patient at one or more SNPs described herein as being associated with one or both of IgE level or tradipitant treatment effect, or alternatively, identifying the patient's IgE level. The methods of identifying said genotype or IgE level may include those methods previously discussed. Based on the identification or determination of the individual's genotype or IgE level, it can be predicted whether the patient is likely to respond favorably to treatment of atopic dermatitis and/or pruritus with tradipitant. For example, if the patient's genotype includes one or more variants associated with a high IgE or with a positive tradipitant treatment response, or if the patient's IgE level is identified as being greater than a threshold value, for example, 50 kU/L, 75 kU/L, 100 kU/L, 150 kU/L, 200 kU/L, or 300 kU/L, then the patient is likely to respond to the tradipitant treatment. However, if the patient's genotype does not include any variants associated with a high IgE or with a positive tradipitant treatment response, or if the patient's IgE level is identified as being less than a threshold value, for example, 50 kU/L, 75 kU/L, 100 kU/L, 150 kU/L, 200 kU/L, or 300 kU/L, then the patient may be deemed to be unlikely or less likely to respond to tradipitant treatment, or less likely to demonstrate a significant respond to the tradipitant treatment. Such information is useful to patients and medical professionals for its value in prospectively identifying patients who will particularly benefit from treatment with tradipitant, and for reducing trial and error attempts to identify a successful therapy, particularly in the case of individuals who are unlikely to respond to tradipitant treatment at a dose of 170 mg/day. Such individuals may benefit from treatment with, e.g., a different active pharmaceutical ingredient, or with a larger dose of tradipitant.

As used herein, the terms "patient" and "individual" refer to a mammal that is afflicted with one or more disorders ameliorated by administration of tradipitant, e.g., atopic dermatitis, pruritus, and pruritus associated with atopic dermatitis. Guinea pigs, dogs, cats, rats, mice, horses, cattle, sheep, and humans are examples of mammals within the scope of the meaning of the term. It will be understood that the most preferred patient is a human.

It is also recognized that one skilled in the art may affect the disorders by treating a patient presently afflicted with the disorders or by prophylactically treating a patient afflicted with the disorders with an effective amount of tradipitant. Thus, the terms "treatment" and "treating" are intended to refer to all processes wherein there may be a slowing, interrupting, arresting, controlling, or stopping of the progression of the diseases or disorders described herein, and is intended to include prophylactic treatment of such disorders, but does not necessarily indicate a total elimination of all disorder symptoms.

As used herein, the term "effective amount" of tradipitant refers to an amount that is effective in treating the disorders described herein.

With regard to dosing, qd refers to dosing once per day; and bid dosing typically means dosing once in the morning and once in the evening, generally no less than about 8 hours or more than about 16 hours apart, e.g., 10 to 14 hours apart, or 12 hours apart (Q12H).

As used herein, the terms "first," "second," and the like, do not denote any order, quantity, or importance, but rather are used to distinguish one element from another, and the terms "a" and "an" herein do not denote a limitation of quantity, but rather denote the presence of at least one of the referenced item. The modifier "about" used in connection with a quantity is inclusive of the stated value and has the meaning dictated by the context (e.g., includes the degree of error associated with measurement of the particular quantity). The suffix "(s)" as used herein is intended to include both the singular and the plural of the term that it modifies, thereby including one or more of that term (e.g., the metal(s) includes one or more metals). Ranges disclosed herein are inclusive and independently combinable (e.g., ranges of "up to about 25 mg, or, more specifically, about 5 mg to about 20 mg," is inclusive of the endpoints and all intermediate values of the ranges of "about 5 mg to about 25 mg," etc.).

The skilled artisan will appreciate that additional preferred embodiments may be selected by combining the preferred embodiments above, or by reference to the examples given herein.

Example 1: Tradipitant Monotherapy for Treatment of Chronic Pruritus in Patients with Atopic Dermatitis A phase II proof of concept clinical study (Study ID VP-VLY-686-2101, "Proof of Concept of VLY-686 in Subjects With Treatment-Resistant Pruritus Associated With Atopic Dermatitis") is conducted, investigating the safety and efficacy of tradipitant as a monotherapy in the treatment of chronic pruritus in patients with atopic dermatitis.

Despite a highly significant and clinically meaningful improvement from baseline by tradipitant (40.5 mm improvement from baseline, $p<0.0001$) as measured on a 100 mm unit Visual Analog Scale (VAS) for itch, a very high placebo effect (36.5 mm improvement from baseline, $p<0.0001$) on the change from baseline leads to no statistical difference from placebo. However, subsequent analysis of population PK samples across all patients in the study reveals significant and clinically meaningful responses across multiple outcomes evaluated in individuals with higher levels of tradipitant exposure at the time of their pruritus assessments.

The pre-specified primary endpoint of the Phase II proof of concept clinical study is the change from baseline on the Visual Analog Scale (VAS) for itch. Due to high placebo effect, there is no significant difference from placebo on this pre-specified endpoint. However, in subsequent analyses it has been discovered that there is an exposure response relationship. It is observed that there is a significant and clinically meaningful response across several pruritus related outcomes evaluated in individuals with higher blood plasma levels of tradipitant. Based on the data examined across the study, lower blood plasma levels of tradipitant may be below a threshold of efficacy to ameliorate the itch sensation in patients.

Methods

In the study, patients with a Visual Analog Scale (VAS) score of greater than 70 mm during one of the two days preceding inclusion into the study are randomized to receive orally either 100 mg of tradipitant (n=34) or placebo (n=35) once a day in the evening. In the tradipitant arm of the study, tradipitant is orally administered to patients in capsules with standard excipients in an amount of 100 mg in the evening. Clinical assessments are made after 3 or 4 weeks of daily treatment, or at both 3 weeks and 4 weeks, each assessment being done in the morning of the day after last treatment or in the afternoon of the day after last treatment. The tradipitant is administered in an immediate release form comprising tradipitant and pharmaceutically acceptable excipients in a capsule. The tradipitant particle size is approximately: $D_{10}$: <5 um, $D_{50}$: <10 um, and $D_{90}$: <25 um, wherein $D_{10}$ means that 10% of the particles are of the indicated mean particle size, $D_{50}$ means that 50% of the particles are of the indicated mean particle size, and $D_{90}$ means that 90% of the particles are of the indicated mean particle size.

Baseline VAS scores are 76.1 and 77.2 for the tradipitant and placebo arms respectively. Efficacy is evaluated through a number of clinical research instruments. In addition, at the time of efficacy evaluation blood samples are collected for PK analysis in order to determine the plasma levels of tradipitant.

Results

Figure 2:
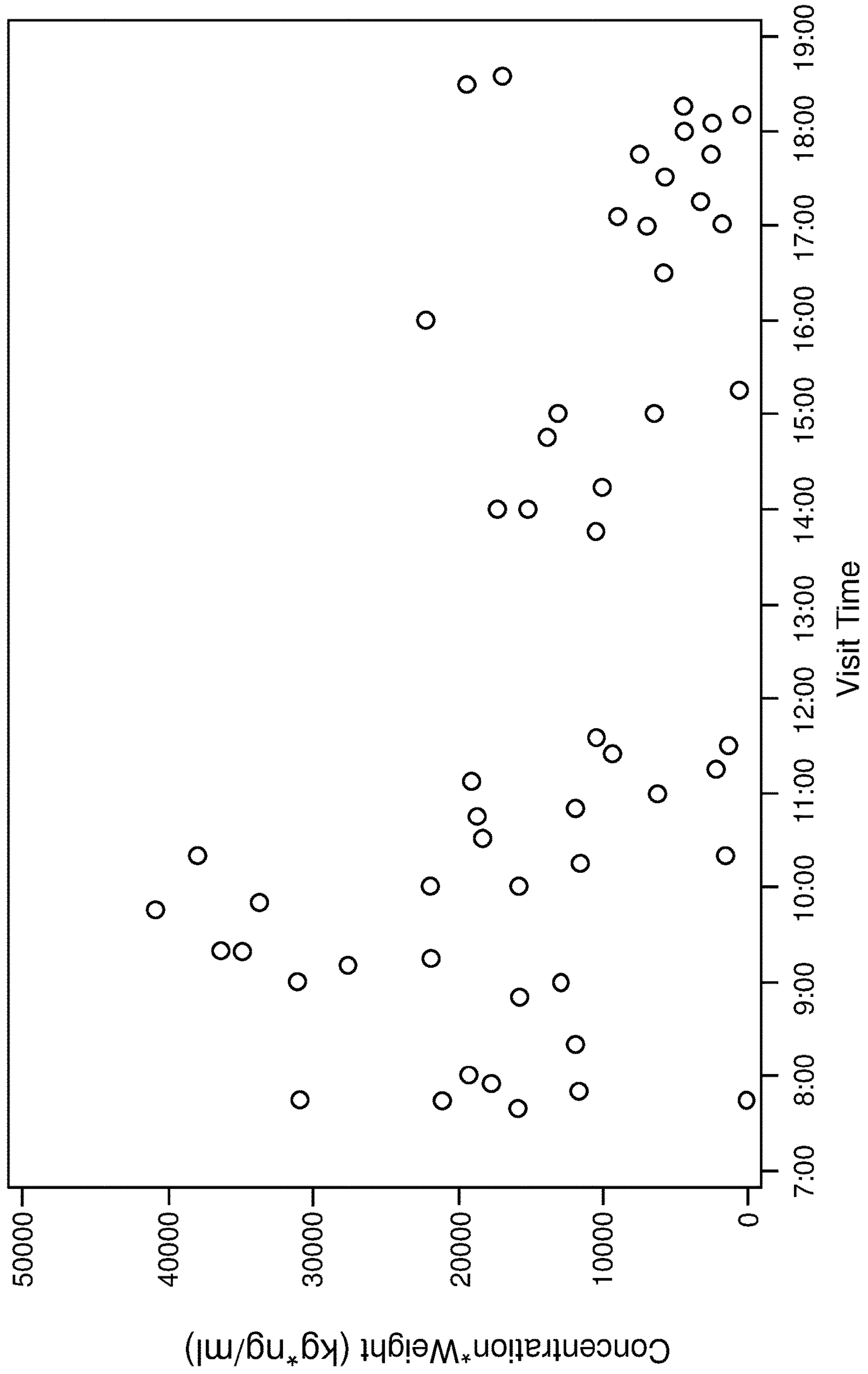
FIG. 2 provides a scatter plot of serum levels of tradipitant, showing concentration weight vs. visit time, as described in Example 1.

As shown in FIG. 1, a PK-PD (pharmacokinetic-pharmacodynamics) analysis in the tradipitant treatment arm shows a significant correlation between blood levels of tradipitant and the VAS change from baseline ($p<0.05$). Individuals with higher circulating levels of tradipitant at the time of the efficacy evaluation demonstrate higher magnitude of response. A separate PK analysis of the time of pruritus assessment, shown in FIG. 2, reveals that approximately half of the patients in the study came in for morning (AM group, ~12 hours post-dose) visits for their pruritus assessments and that these patients also have higher blood levels of tradipitant than those who came in the afternoon (PM group, ~18 hours post-dose).

The average plasma concentrations of tradipitant across AM and PM-evaluated patients are between about 125 ng/mL and about 225 ng/mL. Patients evaluated in the afternoons (PM) (mean=about 20 hours post last administration) tend to have lower plasma concentrations of tradipitant than patients evaluated in the mornings (AM) (mean=about 15 hours post last administration). The average plasma concentration in the PM group is about 125 ng/mL, and the average plasma concentration in the AM group is about 225 ng/mL, the difference being largely attributable to the length of time post-administration. More significantly, the results show a correlation between plasma concentration and efficacy, whereby patients in whom the plasma concentrations are >100 ng/mL (e.g., about 125 ng/mL or greater, about 150 ng/mL or greater, about 175 ng/mL or greater, about 200 ng/mL or greater, or about 225 ng/mL or greater) tend to show greater efficacy than patients with lower plasma concentrations.

A further analysis of the AM group reveals significant and clinically meaningful effects of tradipitant as compared to placebo and is shown in Table 1. Higher concentrations of tradipitant are associated with higher efficacy in treating chronic pruritus in the study. A similar analysis in the PM group shows no significant differences between tradipitant and placebo.

TABLE 1

Group efficacy analysis of pruritus measures

| | AM | | | | PM | | | |
|---|---|---|---|---|---|---|---|---|
| | Tradipitant N = 18 | Placebo N = 17 | Diff | P-value | Tradipitant N = 13 | Placebo N = 11 | Diff | P-value |
| Primary | | | | | | | | |
| VAS Average change | −54 | −30.3 | −23.7 | 0.007 | −28.8 | −34.6 | 5.82 | 0.6701 |
| Secondary | | | | | | | | |
| VAS Worst change | −47.9 | −26 | −21.9 | 0.0302 | −32.3 | −41.3 | 8.99 | 0.5153 |
| VRS change | −1.46 | −0.67 | −0.79 | 0.0496 | −1.29 | −1.16 | −0.13 | 0.7881 |
| DLQI change | −2.52 | −2.87 | 0.35 | 0.8458 | −5.45 | −3.56 | −1.89 | 0.2423 |
| PBI | 1.47 | 0.73 | 0.74 | 0.0393 | 1.01 | 1.4 | −0.39 | 0.4696 |
| CGIC | 2.46 | 3.61 | −1.15 | 0.0497 | 2.47 | 2.29 | 0.19 | 0.7452 |
| SCORAD change | −9.58 | −4.36 | −5.23 | 0.0027 | −6.29 | −7.18 | 0.88 | 0.7061 |

Table 1 abbreviations:
Visual Analog Scale (VAS),
Verbal Rating Scale (VRS),
Dermatology Life Quality Index (DLQI),
Clinical Global Impression of Change (CGI-C),
Patient Benefit Index (PBI),
SCORing Atopic Dermatitis Index (SCORAD).

These data are consistent with the hypothesis that tradipitant, an NK-1R antagonist, may offer symptomatic relief in patients with pruritus (VAS, VRS, SCORAD subjective). Endpoints are also collected in the study that correspond to the underlying disease (SKINDEX, SCORAD objective, EASI and DLQI). These results do not show any significant difference from placebo which would be expected from a drug targeting the symptom of itch in a short-term 4-week study. Importantly, as pruritus, the intractable itching associated with atopic dermatitis, is the major complaint of patients, the effects that are also seen in the CGI-C scale and the PBI scales suggest a recognizable overall clinically meaningful effect from both the clinician and the patient perspective.

Conclusions

These data provide support for the conclusion that in patients suffering pruritus, e.g., pruritus associated with atopic dermatitis, patients can be treated by orally administering tradipitant, e.g., Form IV or Form V (or a pharmaceutically acceptable salt thereof) in amounts and at a dosing frequency required to achieve plasma concentrations of at least about 100 ng/mL, e.g., 125 ng/mL or greater, 150 ng/mL or greater, 175 ng/mL or greater, 200 ng/mL or greater, or 225 ng/mL or greater. Such plasma concentration levels can be achieved, e.g., by orally administering the tradipitant in immediate release solid dosage forms once per day at a higher dose or in immediate release forms with improved bioavailability or in controlled release forms, or by orally administering the tradipitant multiple times per day, e.g., twice or more times per day, at a lower dose in immediate release or controlled release forms. While the study data show that an effective plasma concentration can be achieved at about 12-18 hours, e.g., about 15 hours, post treatment with 100 mg/day tradipitant in solid form in immediate release capsules, it will be appreciated that it may be possible to achieve effective plasma concentrations using different doses and/or different formulations, including but not limited to controlled release formulations.

In conclusion, while the study fails to show an overall effect of the predefined dose of tradipitant for this study, primarily due to the large placebo effect, the study demonstrates a PK-response relationship as well as significant benefits in the group of patients that are evaluated at the time of higher blood concentrations of tradipitant. In this study tradipitant 100 mg qd is well-tolerated and the adverse event profile is mild and similar to placebo.

Treatment of a patient can be continued until the patient's symptoms of pruritus are ameliorated or eliminated, e.g., ameliorated such that the patient is able to function more or less normally during wake time hours and sleep more or less normally during sleep time hours.

As discussed above, data indicate that in patients suffering pruritus, e.g., pruritus associated with atopic dermatitis, patients can be treated by orally administering tradipitant. Further studies demonstrate the safety and efficacy of various dosing regimens.

Example 2: Plasma Concentration Levels of Tradipitant

A study is conducted in which healthy subject participants are orally administered 85 mg tradipitant on study day 3, and then 85 mg tradipitant Q12H on study days 4-16. Plasma concentration levels of tradipitant are measured on each of day 3, day 7, and day 11.

This study illustrates that administration of 85 mg tradipitant qd (on day 3) produces an average plasma concentration over hours 0-12 that is about 50% of the plasma concentration observed in the PM group in Example 1. On days 7 and 11, the average plasma concentration over hours 0-12 following administration of 85 mg bid (specifically, Q12H) tradipitant is about 150% of the plasma concentration observed in the PM group in Example 1. The average plasma concentration over hours 0-12 at each point is determined by dividing the AUC for hours 0-12 (in (hr.)×(ng/mL)) by 12 hours.

These results indicate that in patients suffering pruritus, e.g., pruritus associated with atopic dermatitis, patients can be treated by orally administering tradipitant, e.g., Form IV or Form V (or a pharmaceutically acceptable salt thereof) in an amount of 85 mg bid, e.g., 85 mg Q12H, in order to achieve plasma concentrations that are greater than the 125 ng/mL observed in the PM group in Example 1.

Example 3: Tradipitant Treatment of Chronic Pruritus Associated with Atopic Dermatitis A phase II, multicenter, randomized, double-blind, placebo-controlled clinical study ("Tradipitant in Treatment-resistant Pruritus Associated with Atopic Dermatitis," clinicaltrials.gov Study ID NCT02651714) is conducted to determine the efficacy of tradipitant relative to placebo in reducing chronic pruritus as measured by the VAS.

Methods

Inclusion criteria for the study include chronic (≥6 weeks) itch related to AD that is refractory to treatment by patient history, average itch score by VAS of ≥70 mm (out of 100 mm), verbal response score (VRS) of ≥3 on at least one of the past three days prior to randomization, and a SCORAD of <80. Study demographics are reported in Table 2 below.

TABLE 2

Study demographics

| All Randomized subjects | Tradipitant (n = 84) | Placebo (n = 84) | Total (n = 168) |
|---|---|---|---|
| Gender - n (%) | | | |
| Male | 32 (38.1) | 31 (36.9) | 63 (37.5) |
| Female | 52 (61.9) | 53 (63.1) | 105 (62.5) |
| Age (years) | | | |
| N | 84 | 84 | 168 |
| Mean (SD) | 41.05 (13.139) | 39.13 (13.568) | 40.09 (13.350) |
| Median | 41.82 | 38.42 | 40.36 |
| Min, Max | 18.3, 66.9 | 18.0, 64.1 | 18.0, 66.9 |
| Race - n (%) | | | |
| White | 49 (58.3) | 57 (67.9) | 106 (63.1) |
| Black or African American | 24 (28.6) | 18 (21.4) | 42 (25.0) |
| Asian | 6 (7.1) | 5 (6.0) | 11 (6.5) |
| American Indian or Alaska Native | 0 | 1 (1.2) | 1 (0.6) |
| Native Hawaiian or other Pacific islander | 2 (2.4) | 0 | 2 (1.2) |
| Other | 3 (3.6) | 3 (3.6) | 6 (3.6) |
| Ethnicity - n (%) | | | |
| Hispanic or Latino | 23 (27.4) | 21 (25.0) | 44 (26.2) |
| Not Hispanic or Latino | 61 (72.6) | 63 (75.0) | 124 (73.8) |
| Not reported | 0 | 0 | 0 |
| Unknown | 0 | 0 | 0 |

TABLE 2-continued

| Study demographics | | | |
|---|---|---|---|
| All Randomized subjects | Tradipitant (n = 84) | Placebo (n = 84) | Total (n = 168) |
| BMI category - n (%) | | | |
| <25 mg/kg2 | 29 (34.5) | 31 (36.9) | 60 (35.7) |
| 25 ≤ x < 30 mg/kg2 | 31 (36.9) | 22 (26.2) | 53 (31.5) |
| ≥30 mg/kg2 | 24 (28.6) | 31 (36.9) | 55 (32.7) |

Figure 3:
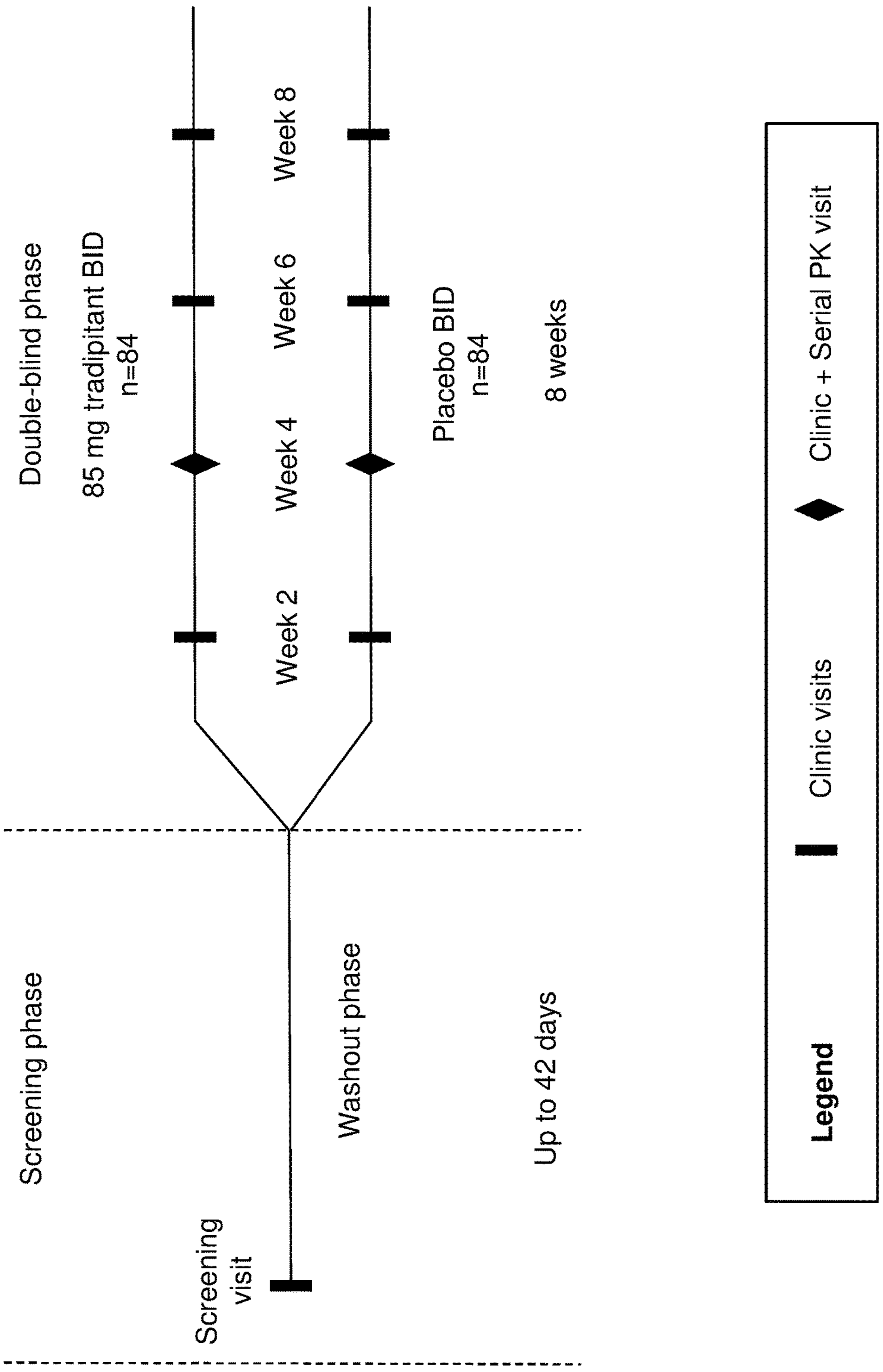
FIG. 3 illustrates the design of the study described in Example 3.

Patients are randomized to receive either 85 mg of tradipitant or placebo (1:1) bid. The design for the randomized, placebo-controlled, double-blind study is depicted in FIG. 3. Individuals with chronic pruritus associated with AD are administered 85 mg of tradipitant bid or placebo for eight weeks. Average itch severity and worst itch severity are assessed by VAS, and VRS is assessed every two weeks. In addition, treatment is assessed biweekly using both the objective and subjective SCORing Atopic Dermatitis (SCORAD) Index (Severity Scoring of Atopic Dermatitis: The SCORAD Index, Consensus Report of the European Task Force on Atopic Dermatitis, Dermatology 1993; 186:23-31) and the Eczema Area and Severity Index (EAST) (Hanifin et al., The eczema area and severity index (EAST): assessment of reliability in atopic dermatitis, Experimental Dermatology 10(1):11-18 (2001)). The Clinical Global Impressions of Change (CGI-C) scale, the Patient Global Impression of Change (PGIC) scale with respect to both itch and AD, the Patient Benefit Index (PBI), and SKINDEX-16 scales are also used for assessments. Twice daily questionnaires are completed to report worst and average itch by numeric rating scale (NRS).

The objective SCORAD assessment includes parameters including extension, intensity, excoriations, erythema, oozing or crusting, the presence of edema or papules, lichenification, and skin dryness. The subjective SCORAD assessment includes patient assessments of itch and insomnia.

Results

As noted, the 168 patients participating in the study are randomized to 85 mg bid tradipitant (n=84) and placebo bid (n=84). Among the 84 patients randomized to the tradipitant arm of the study, 56 patients complete the study with 28 discontinuing. Among the 84 patients randomized to placebo, 59 complete the study with 25 discontinuing.

Figure 4:
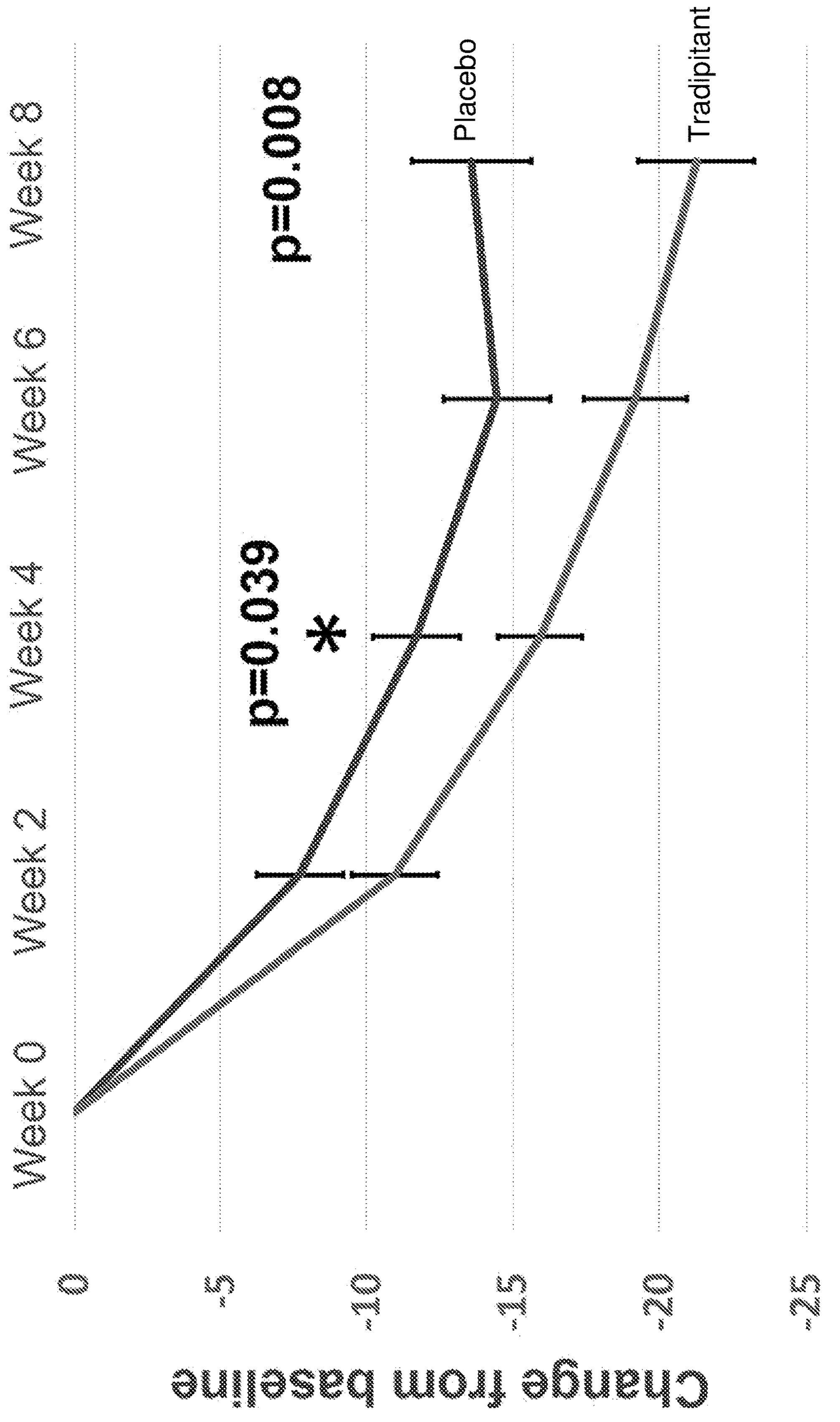
FIG. 4 illustrates time progression vs. itch change from baseline results in the study described in Example 3.
Figure 5:
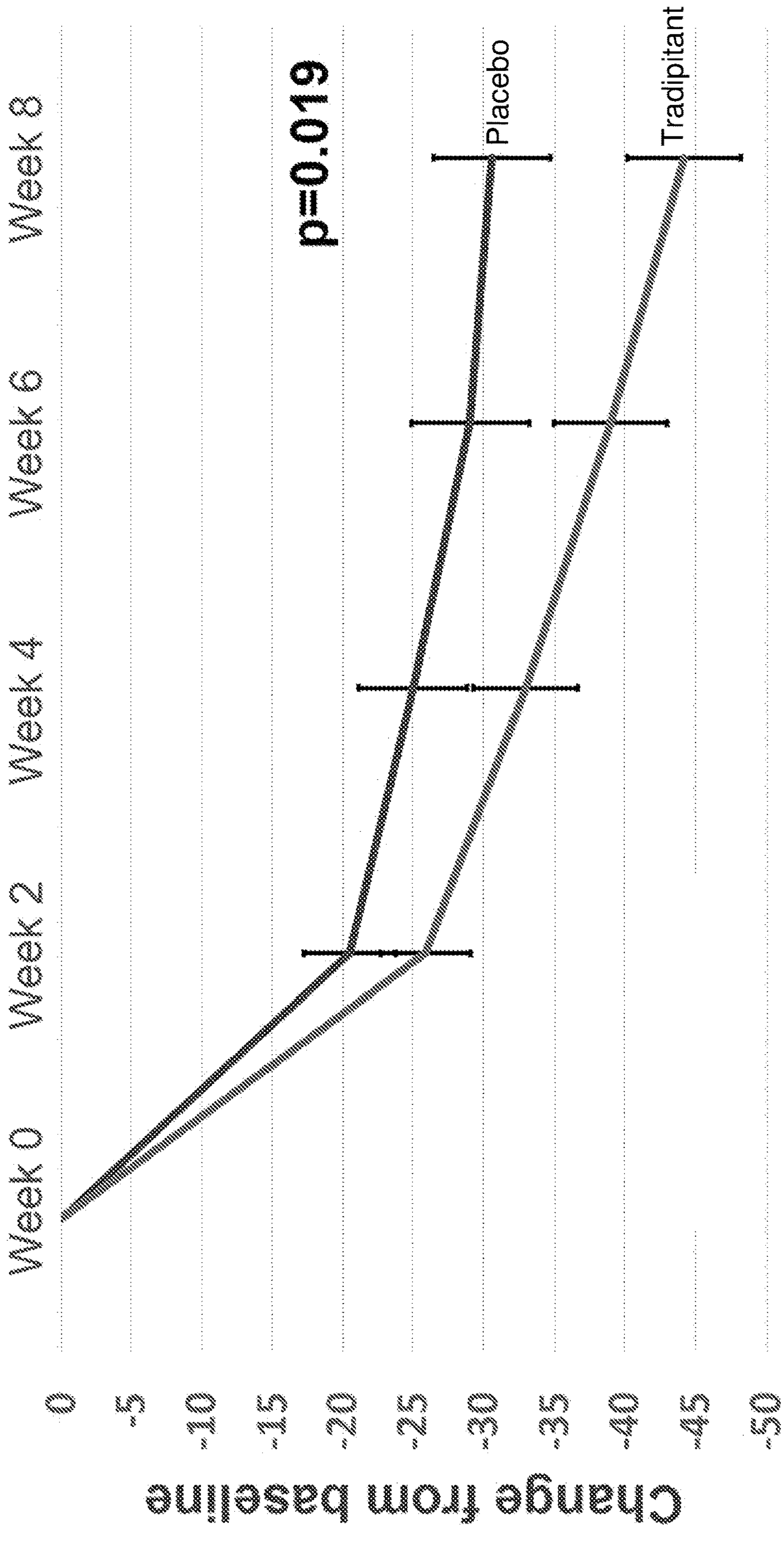
FIG. 5 illustrates time progression vs. disease results in the study described in Example 3.

The results of this study are shown below in Tables 3-4, as well as in FIGS. 4-5. Similar to the AM results of the study described above in Example 1, statistically-significant differences between tradipitant and placebo are observed with respect to worst itch (p=0.019), PBI (p=0.038), CGIC (p=0.007), and the objective SCORAD scale (p=0.005). Additionally, treatment effects in both itch and disease severity are evident as early as Week 2 (FIGS. 4-5). A subset of atopic dermatitis symptoms are collected by daily diary which also demonstrates differences earlier than week 2.

These results also show statistically-significant differences with respect to PGI-C assessments of both itch and AD (p=0.0246 and 0.007, respectively) and the proportion of patients experiencing 50% or greater improvement in SCORAD assessment or 75% or greater improvement in EASI assessment is statistically greater for those patients treated with tradipitant, as compared to placebo.

TABLE 3

| Intent-to-treat analysis at week 8 | | | | |
|---|---|---|---|---|
| Continuous | ITT population | Tradipitant | Placebo | p-value |
| Itch outcomes | | | | |
| | Average itch VAS | −41.5 | −35.8 | 0.306 |
| | Worst itch VAS | −44.2 | −30.6 | 0.019 |
| | Worst itch NRS night | −3.4 | −2.4 | 0.029 |
| | Worst itch NRS day | −3.3 | −2.5 | 0.074 |
| Disease outcomes | | | | |
| | SCORAD total | −21.3 | −13.6 | 0.008 |
| | Objective SCORAD | −13.3 | −7.2 | 0.005 |
| | Subjective SCORAD | −8.1 | −6.7 | 0.157 |
| General Impression Outcomes | | | | |
| | CGI-C | 2.6 | 3.3 | 0.007 |
| | PGI-C Itch | 2.6 | 3.2 | 0.025 |
| | PGI-C AD | 2.7 | 3.4 | 0.007 |
| Quality of life outcomes | | | | |
| | PBI | 1.7 | 1.2 | 0.038 |
| | SKINDEX-16 | −34.8 | −26.6 | 0.102 |
| Categorical | ITT Population | | | |
| Itch Outcomes | | | | |
| | Worst itch VAS ≥ 40 | 52.60% | 34.70% | 0.037 |
| | Worst itch VAS ≥ 30 | 56.60% | 38.90% | 0.049 |
| Disease Outcomes | | | | |
| | SCORAD ≥ 50% | 44.00% | 20.80% | 0.004 |
| | EASI ≥ 75% | 21.10% | 11.10% | 0.067 |

TABLE 4

| Study results of Tradipitant in Treatment-resistant Pruritus Associated with Atopic Dermatitis | | | | |
|---|---|---|---|---|
| | Tradipitant | placebo | difference | p value |
| average itch VAS | −41.5 | −35.8 | −5.7 | 0.306 |
| worst itch VAS | −44.2 | −30.6 | −13.6 | 0.019 |
| worst itch VAS (≥40) | 52.6% | 34.7% | 17.9% | 0.0373 |
| worst itch NRS night | −3.4 | −2.4 | −1.05 | 0.0294 |
| worst itch NRS day | −3.3 | −2.5 | −0.81 | 0.0741 |
| SCORAD total | −21.28 | −13.6 | −7.68 | 0.008 |
| objective SCORAD | −13.33 | −7.23 | −6.1 | 0.005 |
| subjective SCORAD | −8.14 | −6.71 | −1.43 | 0.157 |
| CGIC | 2.6 | 3.3 | −0.7 | 0.007 |
| PGIC itch | 2.56 | 3.17 | −0.6 | 0.0246 |
| PGIC AD | 2.74 | 3.45 | −0.71 | 0.007 |
| PBI | 1.72 | 1.24 | 0.48 | 0.038 |
| SCORAD ≥ 50% | 44.0% | 20.8% | 23.2% | 0.0044 |
| EASI ≥ 75% | 21.1% | 11.1% | 10.0% | 0.0667 |

Conclusions

The results described above show that tradipitant improves the intensity of the worst itch patients experience, as well as atopic dermatitis disease severity. Tradipitant demonstrates significant and clinically meaningful improvement in a number of measures of itch. Specifically, significant improvements are observed in the measurement of Worst Itch Visual Analog Scale (VAS) (p=0.019). Tradipitant also shows significant effects in a responder analysis for Worst Itch in patients who achieve improvements of greater than or equal to 40 points improvement from baseline in Worst Itch VAS scores (p=0.037) or greater than or equal to 30 points (p=0.049). On the pre-specified primary endpoint of Average Itch VAS, tradipitant shows improvement over placebo, but this improvement is not significant due to high placebo effect and the lack of sensitivity of this measure.

Consistent with the observed improvements in Worst Itch, which is associated with scratching behavior, tradipitant also demonstrates disease modifying properties by showing significant improvement in the Total SCORAD scale (p=0.008) and Objective SCORAD scale (p=0.005). Specifically, tradipitant shows significant improvements in several clinical features of severity of atopic dermatitis, including excoriation, erythema, oozing and dryness.

These clinically meaningful effects are also accompanied by significant improvements in the Clinical Global Impression scale—Change (CGI-C) (p=0.007), the Patient Global Impression scale (PGI-C) Itch (p=0.024) the PGI-C AD (p=0.007). Similarly, tradipitant also shows direct patient reported benefits as measured by the Patient Benefit Index scale (PBI) (p=0.037). These improvements, as well as improvements as measured by the EASI assessment (measures the extent (percent coverage in each of four body regions—head and neck, trunk, upper limbs, and lower limbs) and severity of disease (assessing redness, thickness, scratching, and lichenification)) demonstrate the effectiveness of tradipitant in improving measures of underlying AD disease severity in addition to pruritic symptoms.

Example 4: Immunoglobulin E

In the study described above in Example 3, an exploratory analysis is conducted to analyze Immunoglobulin E (IgE) levels and the effect of treatment with tradipitant on atopic dermatitis and pruritus. For purposes of the analysis, study participants having an IgE level greater than or equal to 100 kU/L are deemed to have a high IgE level, while study participants having an IgE level of less than 100 kU/L are deemed to have a low IgE level. The baseline mean and range SCORAD total for each of the total study population, the high IgE group, and the low IgE group are shown below in Table 5.

TABLE 5

Baseline SCORAD measures

| | Treatment Group | N | Mean (SCORAD total) | Std. Dev | (SCORAD total) Range Min | Max |
|---|---|---|---|---|---|---|
| High IgE | Placebo | 37 | 47.81 | 14.03 | 18.33 | 78.32 |
| | Tradiptant | 38 | 50.99 | 13.03 | 24.19 | 79.76 |
| Low IgE | Placebo | 34 | 42.48 | 12.82 | 11.24 | 62.81 |
| | Tradipitant | 35 | 45.12 | 12.91 | 14.04 | 72.92 |
| Total population | | 144 | 46.7 | | 11.2 | 79.76 |

The mean and range of SCORAD totals shown in Table 5 illustrate that the study population spans different strata of disease severity, from mild to severe. Table 5 also illustrates the similarity in disease severity between the high IgE and low IgE groups. Table 6 (below) presents the study results of tradipitant in treatment-resistant pruritus associated with atopic dermatitis in individuals having high baseline IgE levels (IgE≥100 kU/L), while Table 7 (below) presents the study results of tradipitant in treatment-resistant pruritus associated with atopic dermatitis in individuals having low baseline IgE levels (IgE<100 kU/L). The data in Tables 6-7 represent a separation by IgE level of the data appearing in Table 4 above.

TABLE 6

Study results of Tradipitant in Treatment-resistant Pruritus Associated with Atopic Dermatitis in Individuals having a High IgE

| | ITT population | Tradipitant | Placebo | Diff | P-value | |
|---|---|---|---|---|---|---|
| Primary | Average Itch VAS | −41.9 | −26.9 | −14.97 | 0.0678 | |
| Secondary | worst Itch VAS | −43.9 | −18.2 | −25.7 | 0.0020 | |
| | worst ItchVAS >= 40 | 50.0% | 21.6% | 28.4% | 0.0158 | Fisher |
| | worst Itch VAS >= 30 | 57.9% | 21.6% | 36.3% | 0.0020 | Fisher |
| | Average Itch NRS | −3.4 | −1.8 | −1.6 | 0.0072 | |
| | Worst Itch NRS | −3.6 | −1.6 | −2.1 | 0.0012 | |
| | Sleep Disturbance | −3.5 | −1.8 | −1.7 | 0.0086 | |
| | Worst Itch NRS Night | −3.8 | −1.6 | −2.14 | 0.0011 | |
| | Worst Itch NRS Day | −3.7 | −1.6 | −2.06 | 0.0015 | |
| | SCORAD Total | −20.3 | −10.3 | −9.9 | 0.0220 | |
| | Objective SCORAD | −11.7 | −5.4 | −6.4 | 0.0495 | |
| | Extension | −2.4 | −1.6 | −0.72 | 0.7830 | |
| | Intensity | −3.2 | −1.4 | −1.75 | 0.0380 | |
| | Excoriations | −0.80 | −0.24 | −0.56 | 0.0043 | |
| | Erythema | −0.46 | −0.31 | −0.15 | 0.3722 | |
| | Oozing/crusting | −0.53 | −0.30 | −0.23 | 0.1503 | |

TABLE 6-continued

Study results of Tradipitant in Treatment-resistant Pruritus Associated with Atopic Dermatitis in Individuals having a High IgE

| ITT population | Tradipitant | Placebo | Diff | P-value | |
|---|---|---|---|---|---|
| edema/Papules | −0.62 | −0.23 | −0.39 | 0.0501 | |
| Lichenification | −0.42 | −0.15 | −0.27 | 0.1661 | |
| Skin dryness | −0.62 | −0.36 | −0.27 | 0.1727 | |
| Subjective SCORAD | −8.7 | −5.6 | −3.1 | 0.0443 | |
| Itch | −4.7 | −2.7 | −2.04 | 0.0090 | |
| Insomnia | −4.0 | −2.9 | −1.12 | 0.1585 | |
| CGIC | 2.6 | 3.5 | −0.96 | 0.0076 | |
| PGIC ITCH | 2.7 | 3.5 | −0.82 | 0.0447 | |
| PGIC AD | 3.0 | 3.9 | −0.91 | 0.0199 | |
| PBI | 1.7 | 0.99 | 0.67 | 0.0514 | |
| EASI | −3.78 | −2.65 | −1.13 | 0.4814 | |
| Log EASI | −0.8 | −0.35 | −0.46 | 0.0702 | |
| SCORAD 50 | 47.4% | 10.8% | 36.6% | 0.0008 | LOCF |
| EASI 75 | 23.7% | 5.4% | 18.3% | 0.0467 | LOCF |
| VRS | −1.529 | −0.9694 | −0.5597 | 0.0354 | |

TABLE 7

Study results of Tradipitant in Treatment-resistant Pruritus Associated with Atopic Dermatitis in Individuals having low IgE

| | ITT population | Tradipitant | Placebo | Diff | P-value | |
|---|---|---|---|---|---|---|
| Primary | Average Itch VAS | −39.3 | −46.1 | 6.8 | 0.3793 | |
| Secondary | worst Itch VAS | −44 | −43 | −0.9 | 0.9064 | |
| | worst ItchVAS >= 40 | 55.6% | 50.0% | 5.6% | 0.8109 | Fisher |
| | worst Itch VAS >= 30 | 55.6% | 58.8% | −3.2% | 0.8133 | Fisher |
| | Average Itch NRS | −2.9 | −3.4 | 0.4 | 0.5103 | |
| | Worst Itch NRS | −2.9 | −3.2 | 0.3 | 0.6291 | |
| | Sleep Disturbance | −3.0 | −3.0 | 0.2 | 0.8948 | |
| | Worst Itch NRS Night | −3.0 | −3.1 | 0.08 | 0.9089 | |
| | Worst Itch NRS Day | −2.9 | −3.3 | 0.43 | 0.5112 | |
| | SCORAD Total | −19.9 | −17.1 | −2.8 | 0.4569 | |
| | Objective SCORAD | −13.1 | −9.4 | −3.7 | 0.1981 | |
| | Extension | −1.9 | −1.0 | −0.94 | 0.2187 | |
| | Intensity | −3.6 | −2.6 | −0.99 | 0.2241 | |
| | Excoriations | −0.74 | −0.49 | −0.24 | 0.2287 | |
| | Erythema | −0.74 | −0.43 | −0.31 | 0.1098 | |
| | Oozing/crusting | −0.61 | −0.43 | −0.18 | 0.1873 | |
| | edema/Papules | −0.43 | −0.51 | 0.08 | 0.7182 | |
| | Lichenification | −0.49 | −0.46 | −0.03 | 0.8770 | |
| | Skin dryness | −0.73 | −0.33 | −0.40 | 0.0383 | |
| | Subjective SCORAD | −7.2 | −7.6 | 0.43 | 0.7575 | |
| | Itch | −4.0 | −4.2 | 0.13 | 0.8646 | |
| | Insomnia | −3.2 | −3.5 | 0.29 | 0.6783 | |
| | CGIC | 2.7 | 3.1 | −0.3 | 0.3381 | |
| | PGIC ITCH | 2.3 | 2.8 | −0.48 | 0.1563 | |
| | PGIC AD | 2.4 | 3 | −0.6 | 0.1008 | |
| | PBI | 1.98 | 1.47 | 0.5 | 0.1283 | |
| | EASI | −2.7 | −2.23 | −0.47 | 0.5451 | |
| | Log EASI | −0.67 | −0.45 | −0.21 | 0.2749 | |
| | SCORAD 50 | 40.0% | 32.4% | 7.7% | 0.6183 | LOCF |
| | EASI 75 | 19.4% | 17.7% | 1.8% | 1.0000 | LOCF |
| | VRS | −1.54 | −1.31 | −0.23 | 0.3519 | |

The data in Tables 6-7 show results as compared with baseline measures. As illustrated by data in Table 6, in patients with high baseline IgE, tradipitant shows significant effects ($p<0.05$) in most parameters studied including, e.g., Worst Itch and Sleep. Surprisingly, when compared with individuals having low IgE levels (Table 7), the individuals having high IgE levels (Table 6) also show significant treatment effects in atopic dermatitis disease severity measures. In the same analysis at week 8, 47% of tradipitant-treated patients achieve at least a 50 percent reduction of SCORAD (SCORAD 50) as compared to 11% of the placebo treated patients ($p=0.0008$).

For purposes of the present analysis, individuals having an IgE level greater than or equal to 100 kU/L are considered to have high IgE levels, while individuals having an IgE level of less than 100 kU/L are considered to have low IgE levels. Further analyses are also performed, in which individuals having high IgE levels are defined as having IgE levels of greater than or equal to 50 kU/L through greater than or equal to 300 kU/L. In both itch and disease severity, a consistently stronger treatment effect is observed in the high IgE group compared to the low IgE group, regardless of whether the high IgE group is defined by, e.g., IgE≥50 kU/L, ≥100 kU/L, or ≥300 kU/L, and whether the low IgE group is defined by, e.g., IgE<50 kU/L, <100 kU/L, or <300 kU/L. Greater than or equal to 100 kU/L is chosen as the cutoff for the high IgE group for the most detailed analysis (Tables 6-7) as a value that is considered to be the upper limit of normal range for adults by reference labs. Based on these results and extrapolating the normal range in children, a high IgE group in a pediatric population can also be defined for tradipitant effects in itch and disease severity in atopic dermatitis.

From these data, it is concluded that patients with high baseline IgE levels demonstrate a larger effect size on both pruritus and disease severity than patients with low IgE levels. Although 100 kU/L is used as the cutoff for distinguishing between high and low IgE levels in Tables 6-7, it is noted that individuals having IgE levels of, for example, greater than 75 kU/L, greater than 100 kU/L, greater than 150 kU/L, greater than 200 kU/L, 30-700 kU/L, 50-200 kU/L, 100-200 kU/L, or 200-2,000 kU/L may also be considered to have a high IgE levels. Accordingly, individuals having IgE levels of greater than 75 kU/L, greater than 100 kU/L, greater than 150 kU/L, greater than 200 kU/L, 30-700 kU/L, 50-200 kU/L, 100-200 kU/L, or 200-2,000 kU/L may be selected for, e.g., treatment with an NK-1 receptor antagonist such as tradipitant.

Additionally, the foregoing data show that tradipitant has a significant disease-modifying effect relative to atopic dermatitis. This effect is quantifiable using measures such as, for example, IGA, EASI, SCORAD, CGIC, and PGIC, and their respective atopic dermatitis signs and symptoms.

Example 5: Genetic Modifiers of IgE

To identify genetic risk factors which lead to IgE dysregulation, a genome-wide association analysis is conducted using 117 whole genome sequencing atopic dermatitis samples. Using linear regression, the association is directly tested between 14,322,979 single nucleotide polymorphisms (SNPs) and log transformed IgE levels. The most highly significant loci of functional relevance include LRP1B, IL20RA, and IL22RA2 (see Table 8 below).

LRP1B, IL20RA, and IL22RA2 and IgE

The SNPs that are associated with IgE dysregulation include a strong signal within the 6q23 region which contains immune response genes such as Interleukin 20 Receptor Subunit Alpha (IL20RA) and Interleukin 22 Receptor Subunit Alpha (IL22RA2). This family of cytokines may have a pro-inflammatory effect and may have involvement in skin inflammation. Top loci out of this analysis are enriched in cytokine receptor activity and interleukin-20 binding (GO:0042018, GO:0042020).

TABLE 8

Loci associated with log transformed IgE level

| Locus | SNP RSID | chr | Start (hg19) | End (hg19) | Minor allele | Genotype associated with higher IgE | Genotype associated with lower IgE | P value |
|---|---|---|---|---|---|---|---|---|
| LRP1B | rs4575660 | 2 | 142263746 | 142263746 | T | TT | TG/GG | 8.42E−07 |
| LRP1B | . | 2 | 142266867 | 142266867 | G | GG | GA/AA | 8.42E−07 |
| LRP1B | . | 2 | 142266888 | 142266888 | C | CC | CG/GG | 8.42E−07 |
| LRP1B | . | 2 | 142270676 | 142270676 | A | AA | AG/GG | 8.42E−07 |
| LRP1B | . | 2 | 142272120 | 142272120 | T | TT | TC/CC | 2.57E−06 |
| IL20RA, IL22RA2 | rs276555 | 6 | 137415146 | 137415146 | C | CC | CT/TT | 1.42E−07 |
| IL20RA, IL22RA2 | rs74416548 | 6 | 137417398 | 137417398 | AT | ATAT | ATA/AA | 1.78E−08 |
| IL20RA, IL22RA2 | rs276556 | 6 | 137417649 | 137417649 | G | GG | GT/TT | 1.78E−08 |
| IL20RA, IL22RA2 | rs276560 | 6 | 137419637 | 137419637 | C | CC | CT/TT | 1.78E−08 |
| IL20RA, IL22RA2 | rs276561 | 6 | 137419733 | 137419733 | T | TT | TC/CC | 1.78E−08 |
| IL20RA, IL22RA2 | rs276562 | 6 | 137419789 | 137419789 | G | GG | GT/TT | 1.78E−08 |
| IL20RA, IL22RA2 | rs276563 | 6 | 137420361 | 137420361 | C | CC | CT/TT | 5.13E−10 |
| IL20RA, IL22RA2 | rs276563 | 6 | 137420361 | 137420361 | C | CC | CT/TT | 5.13E−10 |
| IL20RA, IL22RA2 | rs276564 | 6 | 137420417 | 137420417 | G | GG | GA/AA | 5.13E−10 |
| IL20RA, IL22RA2 | rs276564 | 6 | 137420417 | 137420417 | G | GG | GA/AA | 5.13E−10 |
| IL20RA, IL22RA2 | rs276571 | 6 | 137426593 | 137426593 | G | GG | GA/AA | 4.57E−09 |
| IL20RA, IL22RA2 | rs140796 | 6 | 137433792 | 137433792 | TATTG | TATTG-TATTG | TATTGT/TT | 5.13E−10 |
| IL20RA, IL22RA2 | rs276573 | 6 | 137433986 | 137433986 | T | TT | TC/CC | 5.13E−10 |
| IL20RA, IL22RA2 | rs276574 | 6 | 137434205 | 137434205 | G | GG | GA/AA | 7.12E−10 |
| IL20RA, IL22RA2 | rs4895474 | 6 | 137434738 | 137434738 | T | TT | TC/CC | 6.60E−06 |
| IL20RA, IL22RA2 | rs4895475 | 6 | 137435023 | 137435023 | G | GG | GA/AA | 6.60E−06 |

TABLE 8-continued

| Loci associated with log transformed IgE level | | | | | | | | |
|---|---|---|---|---|---|---|---|---|
| Locus | SNP RSID | chr | Start (hg19) | End (hg19) | Minor allele | Genotype associated with higher IgE | Genotype associated with lower IgE | P value |
| IL20RA, IL22RA2 | rs9483989 | 6 | 137435667 | 137435667 | T | TT | TG/GG | 6.60E−06 |
| IL20RA, IL22RA2 | rs9373178 | 6 | 137436809 | 137436809 | C | CC | CT/TT | 6.60E−06 |
| IL20RA, IL22RA2 | rs4896234 | 6 | 137437437 | 137437437 | C | CC | CT/TT | 6.68E−05 |
| IL20RA, IL22RA2 | rs2327798 | 6 | 137437988 | 137437988 | G | GG | GA/AA | 1.82E−05 |
| IL20RA, IL22RA2 | rs62420823 | 6 | 137438566 | 137438566 | G | GG | GA/AA | 6.60E−06 |
| IL20RA, IL22RA2 | . | 6 | 137438606 | 137438606 | G | GG | GT/TT | 8.01E−06 |
| IL20RA, IL22RA2 | rs17252967 | 6 | 137438707 | 137438707 | C | CC | CT/TT | 6.60E−06 |
| IL20RA, IL22RA2 | . | 6 | 137439544 | 137439544 | T | TT | TC/CC | 2.21E−05 |
| IL20RA, IL22RA2 | rs9494657 | 6 | 137439915 | 137439915 | A | AA | AG/GG | 6.60E−06 |
| IL20RA, IL22RA2 | rs9402871 | 6 | 137440100 | 137440100 | G | GG | GA/AA | 6.60E−06 |
| IL20RA, IL22RA2 | rs9402872 | 6 | 137440301 | 137440301 | C | CC | CT/TT | 6.60E−06 |
| IL20RA, IL22RA2 | rs9399201 | 6 | 137441113 | 137441113 | G | GG | GA/AA | 6.60E−06 |
| IL20RA, IL22RA2 | rs4896235 | 6 | 137441248 | 137441248 | A | AA | AC/CC | 6.60E−06 |
| IL20RA, IL22RA2 | rs719640 | 6 | 137442746 | 137442746 | A | AA | AG/GG | 6.60E−06 |
| IL20RA, IL22RA2 | . | 6 | 137443924 | 137443924 | G | GG | GA/AA | 8.01E−06 |
| IL20RA, IL22RA2 | . | 6 | 137444356 | 137444356 | G | GG | GT/TT | 8.01E−06 |
| IL20RA, IL22RA2 | rs9373179 | 6 | 137444478 | 137444478 | A | AA | AG/GG | 6.60E−06 |
| IL20RA, IL22RA2 | . | 6 | 137444523 | 137444523 | C | CC | CT/TT | 1.27E−08 |
| IL20RA, IL22RA2 | rs9385784 | 6 | 137445387 | 137445387 | T | TT | TC/CC | 6.60E−06 |
| IL20RA, IL22RA2 | rs2146275 | 6 | 137445769 | 137445769 | A | AA | AC/CC | 6.60E−06 |
| IL20RA, IL22RA2 | rs6941440 | 6 | 137446489 | 137446489 | T | TT | TG/GG | 6.60E−06 |
| IL20RA, IL22RA2 | . | 6 | 137446533 | 137446533 | G | GG | GA/AA | 8.01E−06 |
| IL20RA, IL22RA2 | rs4896237 | 6 | 137447327 | 137447327 | T | TT | TC/CC | 6.60E−06 |
| IL20RA, IL22RA2 | . | 6 | 137447642 | 137447642 | G | GG | GC/CC | 8.01E−06 |
| IL20RA, IL22RA2 | rs6929580 | 6 | 137447736 | 137447736 | G | GG | GC/CC | 6.60E−06 |
| IL20RA, IL22RA2 | rs4896239 | 6 | 137448873 | 137448873 | T | TT | TC/CC | 6.60E−06 |
| IL20RA, IL22RA2 | rs4895479 | 6 | 137448972 | 137448972 | C | CC | CT/TT | 6.60E−06 |
| IL20RA, IL22RA2 | rs4895480 | 6 | 137449229 | 137449229 | T | TT | TG/GG | 6.60E−06 |
| IL20RA, IL22RA2 | rs4280975 | 6 | 137449423 | 137449423 | G | GG | GA/AA | 6.60E−06 |
| IL20RA, IL22RA2 | rs6911523 | 6 | 137452314 | 137452314 | A | AA | AT/TT | 6.60E−06 |
| IL20RA, IL22RA2 | rs6912319 | 6 | 137452537 | 137452537 | G | GG | GT/TT | 6.60E−06 |
| IL20RA, IL22RA2 | . | 6 | 137453707 | 137453707 | C | CC | CT/TT | 3.29E−06 |

Figure 6:
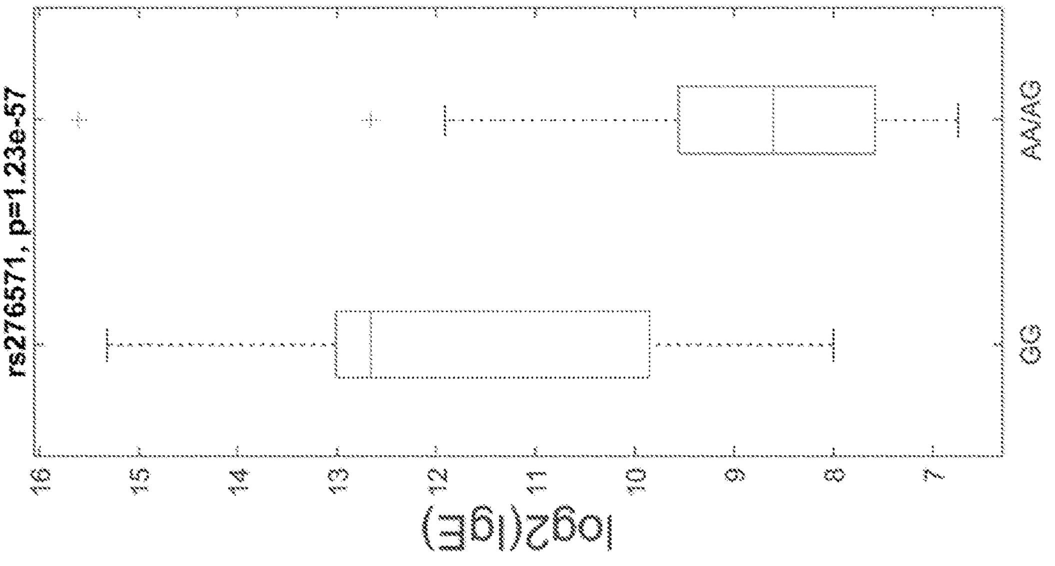
FIG. 6 illustrates the association of the SNP rs276571 with levels of IgE, as described in Example 5.
Figure 7:
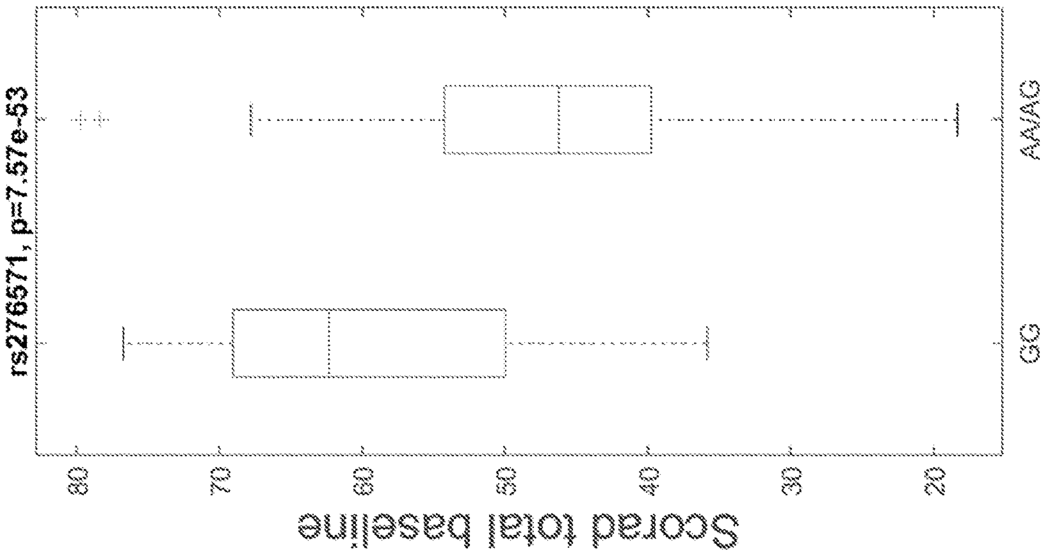
FIG. 7 illustrates the association of the SNP rs276571 with baseline SCORAD, as described in Example 5.

As shown in FIG. 6, the rs276571 SNP (Table 8) is an example of a SNP associated with higher levels of IgE, such that individuals having a GG rs276571 genotype have higher IgE levels than individuals having AG or AA rs276571 genotypes. Additionally, as shown in FIG. 7, the identified variant is not only a modifier of IgE level, but also has a significant effect on baseline SCORAD. Specifically, the GG rs276571 genotype confers significantly higher baseline SCORAD measures of AD disease severity compared with AA or AG rs276571 genotypes. The risk allele is also correlated with higher expression of IL20RA. The rs276571 locus has been shown to be a significant expression quantitative trait locus (eQTL) for IL20RA in genotype tissue expression (GTEx). Table 9, appearing below, provides population frequencies for rs276571 alleles.

TABLE 9

Population frequencies for rs276571

| Population | Allele Count | Allele Number | Number of Homozygotes | Allele Frequency |
|---|---|---|---|---|
| European (Finnish) | 2011 | 3486 | 574 | 0.5769 |
| European (non-Finnish) | 8000 | 14970 | 2110 | 0.5344 |
| Other | 513 | 980 | 131 | 0.5235 |
| East Asian | 839 | 1616 | 232 | 0.5192 |
| Latino | 345 | 838 | 66 | 0.4117 |
| Ashkenazi Jewish | 113 | 302 | 21 | 0.3742 |
| African | 2415 | 8708 | 350 | 0.2773 |
| South Asian | 0 | 0 | 0 | n/a |
| Total | 14236 | 30900 | 3484 | 0.4607 |

Figure 8:
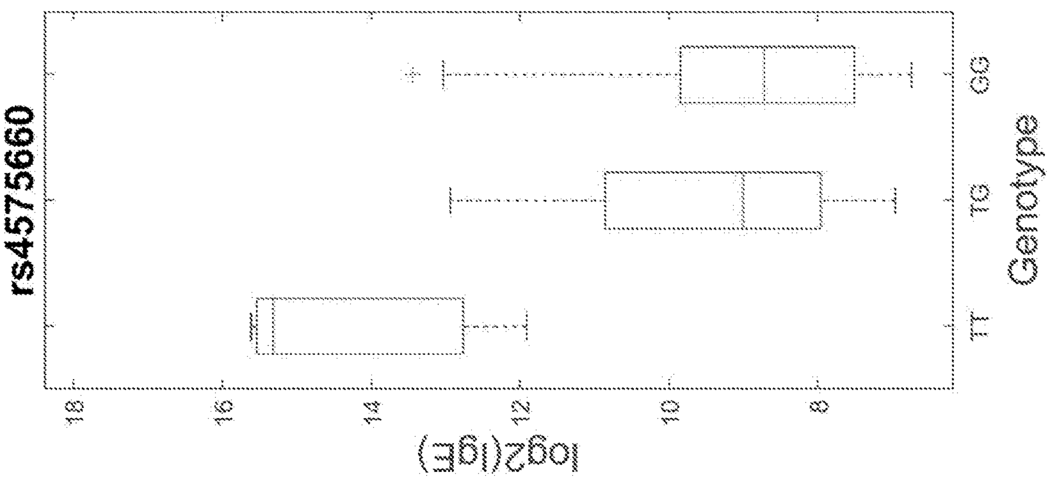
FIG. 8 illustrates the association of the SNP rs4575660 with log transformed IgE levels, as described in Example 5.

Another SNP of interest, rs4575660 (Table 8), found within the LRP1B gene, is also associated with IgE level. As shown in FIG. 8, individuals having a TT rs4575660 genotype have significantly higher IgE levels than individuals having TG or GG rs4575660 genotypes. At the rs4575660 locus, the minor allele confers higher IgE level. As discussed further below, variants in LRP1B are of particular interest due to their association with VAS and SCORAD as discussed in Example 6 (below).

ADAM33 and IgE

Figure 9:
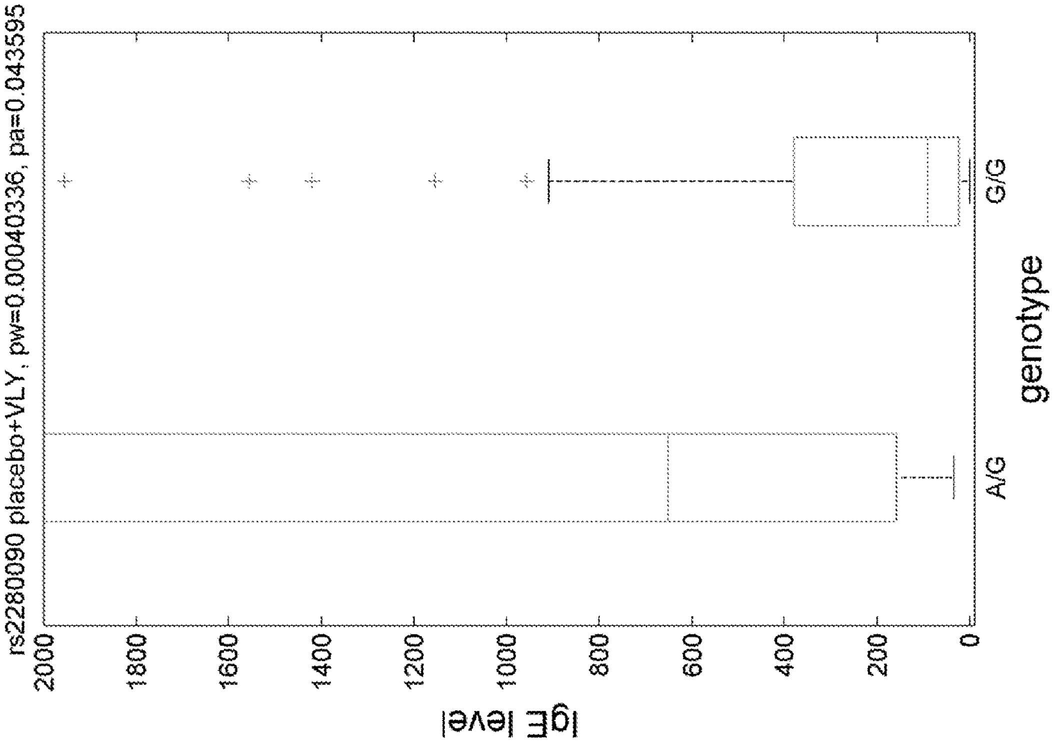
FIG. 9 illustrates the association of the SNP rs2280090 with levels of IgE, as described in Example 5.

Additionally, the missense variant rs2280090, found within a disintegrin and metalloprotease 33 gene (ADAM33), is also associated with IgE dysregulation. As shown in FIG. 9, individuals having heterozygous AG rs2280090 genotypes demonstrate significantly higher IgE levels than individuals having a GG rs2280090 genotype. Among study participants, n=0 individuals having an AA rs2280090 genotype.

Conclusions

As discussed in Example 4 above, individuals with high baseline IgE levels demonstrate a larger tradipitant treatment effect size on both pruritus and AD disease severity than patients with low IgE levels. Therefore, patients suffering from atopic dermatitis whose genotypes include one or more SNP genotypes identified in Table 8 as being associated with a high IgE level can be expected to demonstrate a larger tradipitant treatment effect size on both pruritus and AD disease severity than patients whose gene sequences do not include any of the SNPs identified in Table 8 as being associated with a high IgE.

Example 6: Genetic Markers Correlated with Response to Tradipitant Treatment

A further study is performed to identify additional genetic markers that correlate directly with a positive response to tradipitant treatment. To identify the genetic markers, an association analysis is conducted using a logistic additive model. Visual Analog Scale (VAS) is used as the response outcome metric. The identified variants are shown below in Table 10.

TABLE 10

SNPs associated with VAS response

| Locus | SNP RSID | chr | start (hg19) | end (hg19) | minor allele | major allele | genotypes associated with VAS response | P value | OR |
|---|---|---|---|---|---|---|---|---|---|
| LRP1B | rs16847120 | 2 | 142530945 | 142530945 | T | G | GG | 4.10E−06 | 9.8 |
| MYO10 | rs249122 | 5 | 16922052 | 16922052 | G | A | AA | 2.52E−06 | 9.391 |
| MYO10 | rs6862796 | 5 | 16923669 | 16923669 | T | C | CC | 1.41E−06 | 9.272 |
| MYO10 | rs249137 | 5 | 16929639 | 16929639 | C | T | TT | 4.79E−06 | 7.94 |
| MYO10 | rs249138 | 5 | 16929850 | 16929850 | C | T | TT | 1.41E−06 | 9.272 |
| MYO10 | rs144713688 | 5 | 16944367 | 16944371 | G | GAGAA | GAGAA | 4.72E−06 | 9.684 |
| CTNNA3 | rs73258486 | 10 | 68884892 | 68884892 | G | A | GG/GA | 5.04E−06 | 0.07979 |
| CTNNA3 | rs6480251 | 10 | 68885193 | 68885193 | C | T | CC/CT | 5.04E−06 | 0.07979 |
| CTNNA3 | rs6480252 | 10 | 68885220 | 68885220 | T | C | TT/TC | 5.04E−06 | 0.07979 |
| CTNNA3 | rs10822978 | 10 | 68886829 | 68886829 | T | A | TT/TA | 5.04E−06 | 0.07979 |
| CTNNA3 | rs10997525 | 10 | 68894485 | 68894485 | G | A | GG/GA | 5.04E−06 | 0.07979 |
| CTNNA3 | rs10997527 | 10 | 68898306 | 68898306 | C | A | CC/CA | 5.04E−06 | 0.07979 |
| CTNNA3 | rs7074325 | 10 | 68899950 | 68899950 | C | T | CC/CT | 5.04E−06 | 0.07979 |
| CTNNA3 | rs57930837 | 10 | 68918148 | 68918148 | C | A | CC/CA | 8.80E−07 | 0.05208 |
| CTNNA3 | rs11453660 | 10 | 68934829 | 68934830 | CA | C | CACA/CAC | 5.88E−06 | 0.1234 |
| NRXN3 | rs2199792 | 14 | 79619826 | 79619826 | A | G | AA/AG | 2.72E−06 | 0.1212 |

Figure 11:
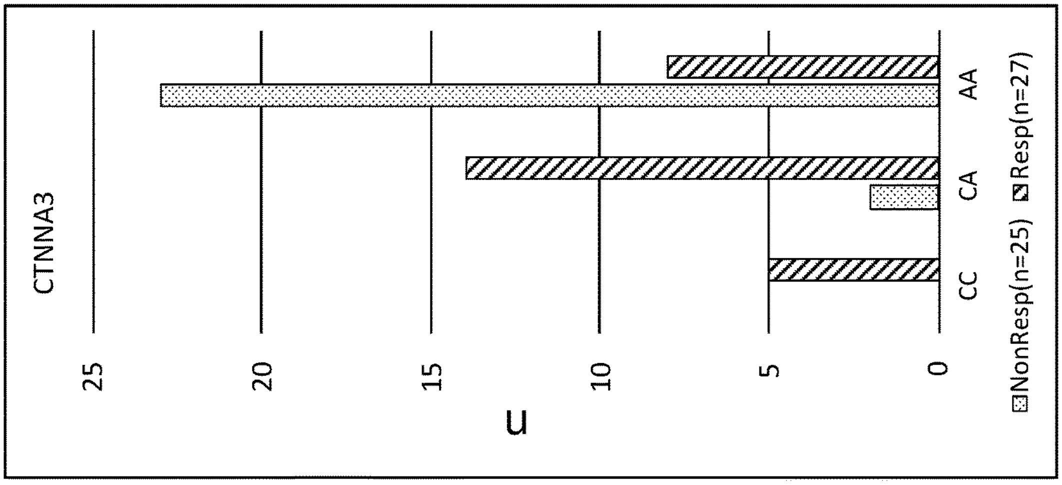
FIG. 11 illustrates the number (n) of responders and non-responders to tradipitant treatment of atopic dermatitis, broken out by CTNNA3 rs57930837 genotype, as described in Example 6.
Figure 10:
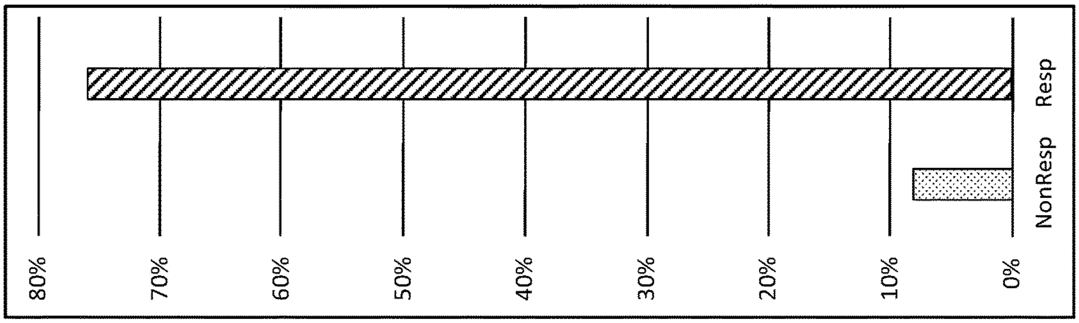
FIG. 10 illustrates the percentage of responders and non-responders to tradipitant treatment of atopic dermatitis among carriers of the CTNNA3 rs57930837 minor allele, as described in Example 6.
Figure 12:
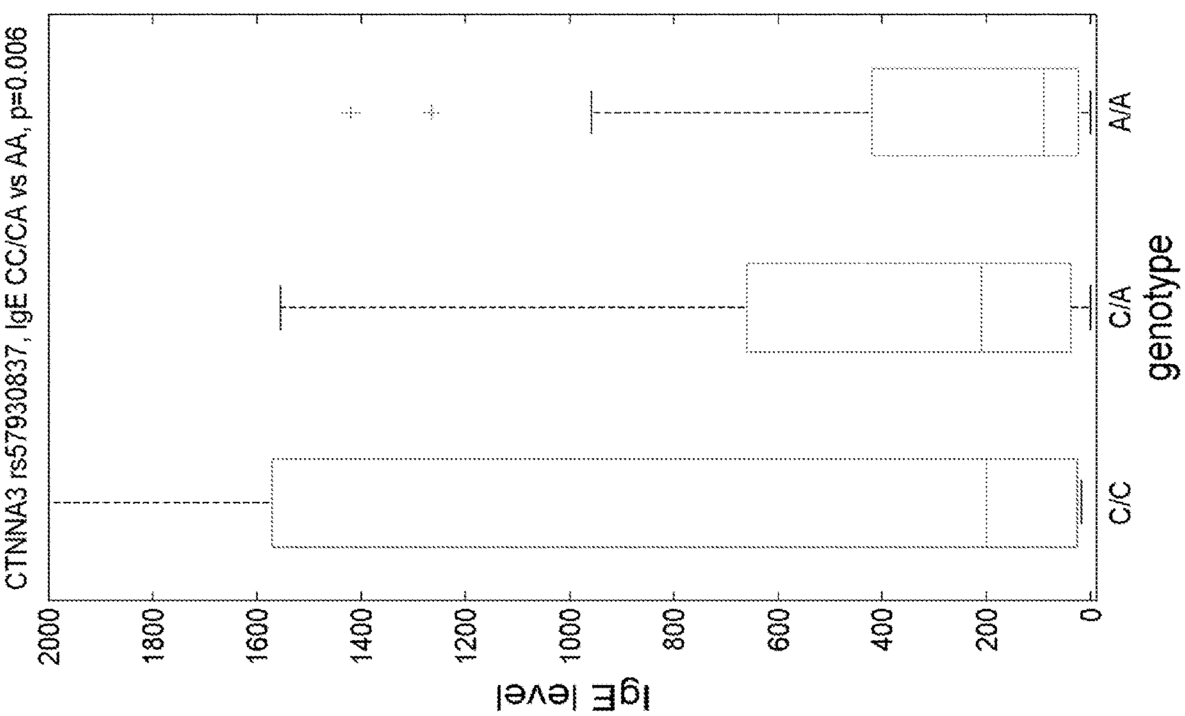
FIG. 12 illustrates the association of CTNNA3 rs57930837 variants with IgE level as described in FIG. 6.

Additionally, a variant in CTNNA3, rs57930837, is found to significantly differentiate between responders and non-responders to tradipitant treatment of atopic dermatitis. As shown in FIG. 10, a majority of carriers of the minor allele demonstrate response to tradipitant treatment of atopic dermatitis, compared to carriers who did not demonstrate response to such treatment. FIG. 11 illustrates the number of responders and non-responders to tradipitant treatment broken out by rs57930837 genotype. As shown, all individuals having a CC rs57930837 genotype respond to treatment, a majority of individuals having a CA rs57930837 genotype respond to treatment, and a majority of rs57930837 AA individuals do not respond to treatment. The rs57930837 variant is found to have an increased minor allele frequency (MAF) (0.44) when compared to controls (0.04). In addition to being a marker of response, a significant difference in IgE level distribution is found between individuals having CC/CA genotypes as compared to AA at this locus, as shown in FIG. 12. This variant reaches the highest level of significance (r557930837, P=$2.19\times10^{-7}$, 7% vs 83%) in this analysis.

In order to evaluate the biological consequences of the top loci distinguishing treatment responders from non-responders, a gene set enrichment analysis is conducted. The other significant loci point to LRP1B (nonsynonymous variant), MYO10, and NRXN3 lipoproteins enriched in low density lipoprotein receptor activity (GO:0005041), and bioactive lipid receptor activity (GO:0045125). The rs57930837 SNP maps to a region of open chromatin, characterized by DNase hypersensitivity, and shows evidence of presence of Foxp1 and other regulatory motifs.

Using the top significant SNPs chosen by p-value cutoff, individuals are classified on responder status to tradipitant treatment, with AUC of 0.95 (10 fold cross validation). Loss of function (LOF) and protein coding variants are investigated in terms of VAS outcomes on the cohort of cases. Significant variants are detected within genes NPSR1, KRTAP1-1, CD200R1L, LRP1B and BTNL2 as shown in Table 11.

Figure 13:
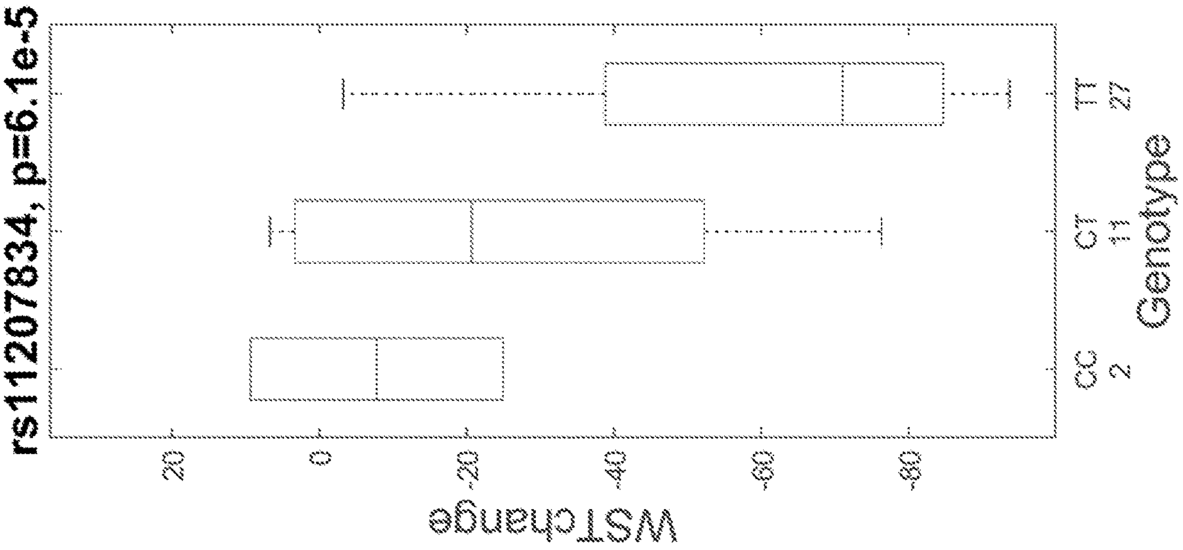
FIG. 13 illustrates the association of INADL rs11207834 variants with Worst Itch change as described in Example 6.

As shown in FIG. 13, the rs11207834 minor allele is associated with decreased response to treatment with 85 mg tradipitant bid, as measured by change of Worst Itch (VAS). In contrast, in patients suffering from atopic dermatitis, whose rs11207834 genotype is TT are associated with itch scale improvement, and such individuals can be expected to demonstrate a larger effect post treatment.

While various embodiments are described herein, it will be appreciated from the specification that various combinations of elements, variations or improvements therein may be made by those skilled in the art, and are within the scope of the invention. In addition, many modifications may be made to adapt a particular situation or material to the teachings of the invention without departing from essential scope thereof. Therefore, it is intended that the invention not be limited to the particular embodiment disclosed, but that the invention will include all embodiments falling within the scope of the appended claims.

TABLE 11

Coding variants associated with VAS response

| Locus | SNP RSID | chr | start (hg19) | end (hg19) | major allele | minor allele | genotypes associated with VAS response | OR | P value |
|---|---|---|---|---|---|---|---|---|---|
| SLC22A24 | rs4963245 | 11 | 62886800 | 62886800 | G | C | CC | 0.09954 | 0.002535 |
| LRP1B | rs12990449 | 2 | 142567910 | 142567910 | T | C | TT | 8.294 | 0.002559 |
| NPSR1 | rs727162 | 7 | 34874038 | 34874038 | C | G | CC | 0.1171 | 0.003272 |
| CD200R1L | rs58161637 | 3 | 112545911 | 112545911 | GT | G | GG | 0.1377 | 0.003716 |
| KRTAP1-3 | rs62622847 | 17 | 39190758 | 39190758 | T | C | CC | 0.09622 | 0.006415 |
| KRTAP1-1 | rs3213755 | 17 | 39197499 | 39197499 | G | A | AA | 0.147 | 0.008684 |
| BTNL2 | rs41521946 | 6 | 32362703 | 32362703 | G | T | TT | 0.1163 | 0.01111 |
| BTNL2 | rs28362678 | 6 | 32362745 | 32362745 | G | A | AA | 0.1163 | 0.01111 |
| BTNL2 | rs35624343 | 6 | 32361762 | 32361762 | G | A | AA | 0.1163 | 0.01111 |
| BTNL2 | rs28362677 | 6 | 32362741 | 32362741 | C | T | TT | 0.1163 | 0.01111 |

In addition, within the treated cohort described herein in Example 4, Table 6, the top loci identified as modifying change of Worst Itch (VAS) are variants located within INADL gene, shown below in Table 12.

TABLE 12

INADL variants

| Locus | SNP RSID | chr | start (hg19) | end (hg19) | minor allele | major allele | genotypes associated with worse Worst Itch (VAS) response | P value |
|---|---|---|---|---|---|---|---|---|
| INADL | rs11207832 | 1 | 62247466 | 62247466 | C | T | CC | 6.08E−05 |
| INADL | rs1954436 | 1 | 62248195 | 62248195 | C | T | CC | 6.08E−05 |
| INADL | rs11207834 | 1 | 62248653 | 62248653 | C | T | CC | 6.08E−05 |
| INADL | rs370530530 | 1 | 62249095 | 62249095 | CT | C | CTCT | 4.90E−05 |
| INADL | rs11207838 | 1 | 62253991 | 62253991 | T | C | TT | 6.08E−05 |
| INADL | rs150980554 | 1 | 62255779 | 62255780 | A | AG | AA | 6.08E−05 |
| INADL | rs7551886 | 1 | 62256251 | 62256251 | C | T | CC | 6.08E−05 |
| INADL | rs6664979 | 1 | 62260512 | 62260512 | C | T | CC | 6.08E−05 |
| INADL | rs12043665 | 1 | 62260524 | 62260524 | A | G | AA | 6.08E−05 |
| INADL | rs12030784 | 1 | 62261898 | 62261898 | T | C | TT | 6.08E−05 |
| INADL | rs79037385 | 1 | 62264128 | 62264128 | G | C | GG | 6.08E−05 |
| INADL | rs74568317 | 1 | 62270403 | 62270403 | C | G | CC | 6.08E−05 |
| INADL | rs3790575 | 1 | 62274531 | 62274531 | C | T | CC | 6.08E−05 |
| INADL | rs77939406 | 1 | 62281618 | 62281618 | G | A | GG | 3.59E−05 |

What is claimed is:

1. In a method consisting of administering an amount of tradipitant effective to treat a patient with pruritus or atopic dermatitis, the improvement comprising:

selecting the patient for treatment based upon:

a) a determination that the patient's genotype includes a genotype associated with a high IgE level, selected from the group consisting of:

rs4575660 TT, rs276555 CC, rs74416548 ATAT, rs276556 GG, rs276560 CC, rs276561 TT, rs276562 GG, rs276563 CC, rs276564 GG, rs276571 GG, rs140796 TATTGTATTG, rs276573 TT, rs276574 GG, rs4895474 TT, rs4895475 GG, rs9483989 TT, rs9373178 CC, rs4896234 CC, rs2327798 GG, rs62420823 GG, rs17252967 CC, rs9494657 AA, rs9402871 GG, rs9402872 CC, rs9399201 GG, rs4896235 AA, rs719640 AA, rs9373179 AA, rs9385784 TT, rs2146275 AA, rs6941440 TT, rs4896237 TT, rs6929580 GG, rs4896239 TT, rs4895479 CC, rs4895480 TT, rs4280975 GG, rs6911523 AA, rs6912319 GG, rs2280090 non-GG, and rs57930837 non-AA, or b) a determination that the patient has a level of IgE of greater than or equal to 100 kU/L.

2. The improvement according to claim 1, wherein the patient is selected for treatment based upon the determination in b), and the patient has a level of IgE of greater than or equal to: 150 kU/L, 200 kU/L, or 300 kU/L.

3. The improvement according to claim 1, further comprising internally administering tradipitant to the patient at a dose of 100-400 mg/day.

4. The improvement according to claim 3, further comprising internally administering tradipitant to the patient at a dose of 100-300 mg/day.

5. The improvement according to claim 4, further comprising internally administering tradipitant to the patient at a dose of 100-200 mg/day.

6. The improvement according to claim 5, further comprising internally administering tradipitant to the patient at a dose of 170 mg/day.

7. The improvement according to claim 6, further comprising internally administering tradipitant to the patient at a dose of 85 mg bid.

8. An improved method for treating a patient suffering from pruritus or atopic dermatitis with tradipitant comprising:

selecting a dosage of tradipitant effective for treating the patient based upon identifying a) the patient's genotype at one or more SNP that is associated with IgE level or with tradipitant treatment effect, or b) the patient's baseline IgE level;

wherein if the patient has a) a genotype associated with a high IgE level or with a positive response to treatment with tradipitant or b) a baseline IgE level greater than about 100 kU/L, then internally administering tradipitant to the patient at a dose of 170 mg/day, and if the patient has a) a genotype that is not associated with a high IgE level or a positive response to treatment with tradipitant and b) a baseline IgE level that is not greater than about 100 kU/L, then internally administering tradipitant to the patient at a dose of greater than 170 mg/day.

9. The method according to claim 8, wherein identifying the patient's genotype in a) further comprises identifying the patient's genotype at a SNP that is associated with a high IgE level, and the SNP is selected from the group consisting of:

rs4575660, rs276555, rs74416548, rs276556, rs276560, rs276561, rs276562, rs276563, rs276563, rs276564, rs276564, rs276571, rs140796, rs276573, rs276574, rs4895474, rs4895475, rs9483989, rs9373178, rs4896234, rs2327798, rs62420823, rs17252967, rs9494657, rs9402871, rs9402872, rs9399201, rs4896235, rs719640, rs9373179, rs9385784, rs2146275, rs6941440, rs4896237, rs6929580, rs4896239, rs4895479, rs4895480, rs4280975, rs6911523, rs6912319, rs2280090, and rs57930837.

10. The method according to claim 9, wherein the genotype associated with a high IgE level is selected from the group consisting of:

rs4575660 TT, rs276555 CC, rs74416548 ATAT, rs276556 GG, rs276560 CC, rs276561 TT, rs276562 GG, rs276563 CC, rs276564 GG, rs276571 GG, rs140796 TATTGTATTG, rs276573 TT, rs276574 GG, rs4895474 TT, rs4895475 GG, rs9483989 TT, rs9373178 CC, rs4896234 CC, rs2327798 GG, rs62420823 GG, rs17252967 CC, rs9494657 AA, rs9402871 GG, rs9402872 CC, rs9399201 GG, rs4896235 AA, rs719640 AA, rs9373179 AA, rs9385784 TT, rs2146275 AA, rs6941440 TT, rs4896237 TT, rs6929580 GG, rs4896239 TT, rs4895479 CC, rs4895480 TT, rs4280975 GG, rs6911523 AA, rs6912319 GG, rs2280090 non-GG, and rs57930837 non-AA.

11. The method according to claim 8, wherein identifying the patient's genotype in a) further comprises identifying the patient's genotype at a SNP that is associated with a positive response to treatment with tradipitant, and the SNP is selected from the group consisting of:

rs16847120, rs249122, rs6862796, rs249137, rs249138, rs144713688, rs73258486, rs6480251, rs6480252, rs10822978, rs10997525, rs10997527, rs7074325, rs57930837, rs11453660, rs2199792, rs4963245, rs12990449, rs727162, rs58161637, rs62622847, rs3213755, rs41521946, rs28362678, rs35624343, rs28362677, rs11207832, rs1954436, rs11207834, rs370530530, rs11207838, rs150980554, rs7551886, rs6664979, rs12043665, rs12030784, rs79037385, rs74568317, rs3790575, and rs77939406.

12. The method according to claim 11, wherein the genotype in a) that is associated with a positive response to treatment with tradipitant is selected from the group consisting of:

rs16847120 GG, rs249122 AA, rs6862796 CC, rs249137 TT, rs249138 TT, rs144713688 GAGAA, rs73258486 GG/GA, rs6480251 CC/CT, rs6480252 TT/TC, rs10822978 TT/TA, rs10997525 GG/GA, rs10997527 CC/CA, rs7074325 CC/CT, rs57930837 CC/CA, rs11453660 CACA/CAC, rs2199792 AA/AG, rs4963245 non-CC, rs12990449 non-TT, rs727162 non-CC, rs58161637 non-GG, rs62622847 non-CC, rs3213755 non-AA, rs41521946 non-TT, rs28362678 non-AA, rs35624343 non-AA, rs28362677 non-TT, rs11207832 non-CC, rs1954436 non-CC, rs11207834 non-CC, rs370530530 non-CTCT, rs11207838 non-TT, rs150980554 non-AA, rs7551886 non-CC, rs6664979 non-CC, rs12043665 non-AA, rs12030784 non-TT, rs79037385 non-GG, rs74568317 non-CC, rs3790575 non-CC, and rs77939406 non-GG.

13. The method according to claim 8, wherein identifying the patient's baseline IgE level in b) further comprises testing a biological sample from the patient to determine an amount of IgE in the biological sample.

14. The method according to claim 8, wherein the dose of greater than 170 mg/day comprises greater than 170 mg/day to 340 mg/day.

15. The method according to claim 14, wherein the dose of greater than 170 mg/day to 340 mg/day comprises greater than 170 mg/day to 255 mg/day.

16. The method according to claim 8, wherein the patient has a baseline IgE level greater than about 150 kU/L and the dose is 170 mg/day.

17. The method according to claim 8, wherein the dose of 170 mg/day is given as 85 mg twice daily (bid).

18. The method according to claim 16, wherein the patient has a baseline IgE level greater than about 200 kU/L and the dose is 170 mg/day.

19. In a method consisting of administering an amount of tradipitant effective to treat a patient with pruritus or atopic dermatitis, the improvement comprising:

selecting the patient for treatment based upon:

a) a determination that the patient's genotype includes a genotype associated with a positive tradipitant treatment response, selected from the group consisting of: rs16847120 GG, rs249122 AA, rs6862796 CC, rs249137 TT, rs249138 TT, rs144713688 GAGAA, rs73258486 GG/GA, rs6480251 CC/CT, rs6480252 TT/TC, rs10822978 TT/TA, rs10997525 GG/GA, rs10997527 CC/CA, rs7074325 CC/CT, rs57930837 CC/CA, rs11453660 CACA/CAC, rs2199792 AA/AG, rs4963245 non-CC, rs12990449 non-TT, rs727162 non-CC, rs58161637 non-GG, rs62622847 non-CC, rs3213755 non-AA, rs41521946 non-TT, rs28362678 non-AA, rs35624343 non-AA, rs28362677 non-TT, rs11207832 non-CC, rs1954436 non-CC, rs11207834 non-CC, rs370530530 non-CTCT, rs11207838 non-TT, rs150980554 non-AA, rs7551886 non-CC, rs6664979 non-CC, rs12043665 non-AA, rs12030784 non-TT, rs79037385 non-GG, rs74568317 non-CC, rs3790575 non-CC, and rs77939406 non-GG, or b) a determination that the patient has a level of IgE of greater than or equal to 100 kU/L.

20. The improvement according to claim 19, further comprising internally administering tradipitant to the patient at a dose of 100-400 mg/day.

* * * * *